US006678619B2

(12) United States Patent
Lobanov et al.

(10) Patent No.: US 6,678,619 B2
(45) Date of Patent: Jan. 13, 2004

(54) METHOD, SYSTEM, AND COMPUTER PROGRAM PRODUCT FOR ENCODING AND BUILDING PRODUCTS OF A VIRTUAL COMBINATORIAL LIBRARY

(76) Inventors: Victor S. Lobanov, 1002 Darby Dr., Yardley, PA (US) 19067; Dimitris K. Agrafiotis, 660 Perimiter Dr., Downingtown, PA (US) 19335; Francis R. Salemme, 1970 Timber Lakes Dr., Yardley, PA (US) 19067

( * ) Notice: Subject to any disclaimer, the term of this patent is extended or adjusted under 35 U.S.C. 154(b) by 106 days.

(21) Appl. No.: 09/956,252

(22) Filed: Sep. 20, 2001

(65) Prior Publication Data

US 2002/0045991 A1 Apr. 18, 2002

Related U.S. Application Data

(60) Provisional application No. 60/234,206, filed on Sep. 20, 2000.

(51) Int. Cl.[7] ............................................... G01N 33/50
(52) U.S. Cl. ................................. 702/32; 435/DIG. 51
(58) Field of Search ............................. 702/32, 22, 23, 702/26, 27, 30; 700/266; 435/DIG. 51; 707/103 R

(56) References Cited

U.S. PATENT DOCUMENTS

| 5,047,929 | A | | 9/1991 | Fujita |
| 5,880,972 | A | | 3/1999 | Horlbeck |
| 5,901,069 | A | | 5/1999 | Agrafiotis et al. |
| 6,240,374 | B1 | * | 5/2001 | Cramer et al. ................. 703/11 |
| 6,319,668 | B1 | * | 11/2001 | Nova et al. ..................... 435/6 |
| 6,507,945 | B1 | * | 1/2003 | Rust et al. .................... 717/103 |

FOREIGN PATENT DOCUMENTS

| EP | 0 818 744 A2 | 1/1998 | ........... G06F/17/50 |
| EP | 0829810 A1 | 3/1998 | |
| WO | WO 93/20242 | 10/1993 | ............ C12Q/1/70 |
| WO | WO 94/28504 | 12/1994 | ........... G06F/15/60 |
| WO | WO 95/01606 | 1/1995 | ........... G06F/15/42 |
| WO | WO 97/27559 | 7/1997 | ........... G06F/19/00 |
| WO | WO 98/20437 | 5/1998 | ........... G06F/17/50 |
| WO | WO 98/20459 | 5/1998 | ........... G06T/11/20 |
| WO | WO 99/59061 | 11/1999 | |

OTHER PUBLICATIONS

Cramer, Richard D. et al., "Virtual Compound Libraries: A New Approach to Decision Making in Molecular Discovery Research," *J. Chem. Inf. Comput. Sci.* 38(6):1010–1023, American Chemical Society (Mar. 1998).

James, Craig A. et al., *Daylight Theory Manual—Daylight 4.71—Jul. 15, 2000 Version*, Daylight Chemical Information Systems, Inc., Mission Viejo, California, USA (2000).

Borg, Ingwer and Groenen, Patrick, *Modern Multidimensional Scaling Theory and Applications*, Springer Series in Statistics, 1997, entire book submitted.

Agrafiotis, D.K. et al., "Advances in diversity profiling and combinatorial series design," *Molecular Diversity*, Kluwer Academic Publishers, vol. 4, 1999, pp. 1–22.

(List continued on next page.)

*Primary Examiner*—Marc S. Hoff
*Assistant Examiner*—Edward Raymond

(57) ABSTRACT

The present invention provides a method, system, and computer program product for encoding and building products of a virtual combinatorial library. A chemical reaction and reagent data for forming products of the virtual combinatorial library are encoded in a computer readable form. A compiler then operates on the encoded information and generates reagent mapping data. The compiler compiles the encoded chemical reaction to genenerate computer instructions that control the operation of a processor. A compact data structure containing data is generated and stored in a memory. This data structure is then used to gain immediate access to any of the products of the virtual combinatorial library.

32 Claims, 19 Drawing Sheets

OTHER PUBLICATIONS

Agrafiotis, D.K. and Lobanov, V.S., "An Efficient Implementation of Distance–Based Diveristy Measures Based on k–d Trees," *Journal of Chemical Information and Computer Science*, American Chemical Society, vol. 39, No. 1, Jan./Feb. 1999, pp. 51–58.

Agrafiotis, D.K. and Lobanov, V.S., "Bridging The Gap Between Diversity And QSAR," *Abstracts of Papers Part 1: 215th ACS National Meeting*, American Chemical Society, Mar. 29–Apr. 2, 1998, p. 181–COMP.

Agrafiotis, D.K. and Jaeger, E.P., "Directed Diversity®: An Operating System For Combinatorial Chemistry," *Abstracts of Papers Part 1: 211th ACS National Meeting*, American Chemical Society, Mar. 24–28, 1996, p. 46–COMP.

Agrafiotis, D.K., "Diversity of Chemical Libraries," *Encyclopedia of Computational Chemistry*, John Wiley & Sons Ltd, vol. 1:A–D, 1998, pp. 742–761.

Agrafiotis, D.K., "On the Use of Information Theory for Assessing Molecular Diversity," *Journal of Chemical Information and Computer Science*, American Chemical Society, vol. 37, No. 3, May/Jun. 1997, pp. 576–580.

Agrafiotis, D.K. et al., "Parallel QSAR," *Abstracts of Papers Part 1: 217th ACS National Meeting*, Mar. 21–25, 1999, p. 50–COMP.

Agrafiotis, D.K. et al., "PRODEN: A New Program for Calculating Integrated Projected Populations," *Journal of Computational Chemistry*, John Wiley & Sons, Inc., vol. 11, No. 9, Oct. 1990, pp. 1101–1110.

Agrafiotis, D.K. and Jaeger, E.P., "Satochastic Algorithms for Exploring Molecular Diversity," *Abstracts of Papers Part 1: 213th ACS National Meeting*, American Chemical Society, Apr. 13–17, 1997, p. 16–CINF.

Agrafiotis, D., "Theoretical Aspects of the Complex: Arts and New Technologies," *Applications and Impacts Information Processing '94*, North–Holland, vol. II, 1994, pp. 714–719.

Biswas, G. et al., "Evaluation of Projection Algorithms," *IEEE Transactions On Pattern Analysis And Machine Intelligence*, IEEE Computer Society, vol. PAMI–3, No. 6, Nov. 1981, pp. 701–708.

Bonchev, D. and Trinajstić, N., "Information theory, distance matrix, and molecular branching," *The Journal of Chemical Physics*, American Institute of Physics, vol. 67, No. 10, Nov. 15, 1977, pp. 4517, 4520–4533.

Chang, C.L. and Lee, R.C.T., "A Heuristic Relaxation Method for Nonlinear Mapping in Cluster Analysis," *IEEE Transactions on Systems, man, and Cybernetics*, IEEE Systems, Man, and Cybernetics Society, vol. SMC–3 Mar. 1973, pp. 197–200.

Kim, J. et al., "Multiple Neural Networks using the Reduced Input Dimension," *Proceedings of the International Conference on Acoustics, Speech, and Signal Processing*, IEEE, vol. 2, Apr. 19–22, 1994, pp. 11–601 to 11–604.

DeMers, D. and Cottrell, G., "Non–Linear Dimensionality Reduction," *Advances in Neural Information Processing Systems*, vol. 5, 1993, pp. 580–587.

Frey, P.W. and Slate, D.J., "Letter Recognition Using Holland–Style Adaptive Classifiers," *Machine Learning*, Kluwer Academic Publishers, vol. 6, 1991, pp. 161–182.

Friedman, J.H., "Exploratory Projection Pursuit," *Journal of the American Statistical Association*, American Statistical Association, vol. 82, No. 397, Mar. 1987, pp. 249–266.

Friedman, J.H. and Tukey, J.W., "A Projection Pursuit Algorithm for Exploratory Data Analysis," *IEEE Transactions on Computers*, IEEE Computer Society, vol. C–23, No. 9, Sep. 1974, pp. 881–889.

Garrido, L. et al., "Use of Multilayer Feedforward neural Nets As A Display Method for Multidimensional Distributions," *International Journal of Neural Systems*, World Scientific Publishing Co. Pte. Ltd., vol. 6, No. 3, Sep. 1995, pp. 273–282.

Ghose, A.K. et al., "Prediction of Hydrophobic (Lipophilic) Properties of Small Organic Molecules Using Fragmental methods: An Analysis of ALOGP and CLOGP Methods," *Journal of Physical Chemistry*, American Chemical Society, vol. 102, No. 21, May 21, 1998, pp. 3762–3772.

Hall, L.H. and Kier, L.B., "The Molecular Connectivity Chi Indexes and Kappa Shape Indexes in Structure–Property Modeling," *Reviews in Computational Chemistry: Advances*, VCH Publishers, Inc., 1991, pp. 367–422.

Hecht–Nielsen, R., "Replicator Neural Networks for Universal Optimal Source Coding," *Science*, American Association for the Advancement of Science, vol. 269, Sep. 29, 1995, pp. 1860–1863.

Hotelling, H., "Analysis of a Complex of Statistical Variables into Principal Components," *The Journal of Educational Psychology*, Warwick and York, Inc., vol. XXIV, No. 6, Sep. 1933, pp. 417–441.

Hotelling, H., "Analysis of a Complex of Statistical Variables into Principal Components," *The Journal of Educational Psychology*, Warwick and York, Inc., vol. XXIV, No. 7, Oct. 1933, pp. 498–520.

Lee, R.C.T. et al., "A Triangulation Method for the Sequential Mapping of Points from N–Space to Two–Space," *IEEE Transactions on Computers*, The Institute of Electrical and Electronics Engineers, Mar. 1977, pp. 288–292.

Lipinski, C.A. et al., "Experimental and computational approaches to estimate solubility and permeability in drug discovery and development settings," *Advanced Drug Delivery Reviews*, Elsevier Science B.V., vol. 23, 1997, pp. 3–25.

Lobanov, V.S. and Agrafiotis, D.K., "Intelligent Database Mining Techniques," *Abstracts of Papers Part 1: 215th ACS National Meeting*, Mar. 29–Apr. 2, 1998, p. 19–COMP.

Lobanov, V.S. et al., "Rational Selections from Virtual Libraries," *Abstracts of Papers Part 1: 217th ACS National Meeting*, Mar. 21–25, 1999, p. 181–COMP.

Mao, J. and Jain, A.K., "Artificial Neural Networks for Feature Extraction and Multivariate Data Projection," *IEEE transactions on Neural Networks*, IEEE Neural Networks, vol. 6, No. 2, Mar. 1995, pp. 296–317.

Oja, E., "Principal Components, Minor Components, and Linear Neural Networks," *Neural Networks*, Pergamon Press Ltd., vol. 5, 1992, pp. 927–935.

Patterson, D.E. et al., "Neighborhood Behavior: A Useful Concept for Validation of 'Molecular Diversity' Descriptors," *Journal of Medicinal Chemistry*, American Chemical Society, vol. 39, No. 16, 1996, pp. 3049–3059.

Pykett, C.E., "Improving the Efficiency of Sammon's Nonlinear Mapping by Using Clustering Archetypes," *Electronics Letters*, The Institution of Electrical Engineers, vol. 14, No. 25, Dec. 7, 1978, pp. 799–800.

Rubner, J. and Tavan, P., "A Self–Organizing Network for Principal–Component Analysis," *Europhysics Letters*, European Physical Society, vol. 10, No. 7, Dec. 1, 1989, pp. 693–698.

Sadowski, J. et al., "Assessing Similarity and Diversity of Combinatorial Libraries by Spatial Autocorrelation Functions and Neural Networks," *Angewandte Chemie*, VCH, vol. 34, No. 23/24, Jan. 5, 1996, pp. 2674–2677.

Spellmeyer, D. et al., "Conformational analysis using distance geometry methods," *Journal of Molecular Graphics & Modelling*, Elsevier Science, Inc., vol. 15, No. 1, Feb. 1997, pp. 18–36.

Barnard, John M. and Downs, Geoff M., "Computer representation and manipulation of combinatorial libraries," *Perspectives in Drug Discovery and Design*, Kluwer Academic Publishers, 1997, pp. 13–30.

Brint, Andrew T. and Willett, Peter, "Upperbound procedures for the identification of similar three–dimensional chemical structures," *Journal of Computer–Aided Molecular Design*, ESCOM Science Publishers B.V., vol. 2, No. 4, Jan. 1989, pp. 311–320.

Brown, Robert D. and Martin, Yvonne C., "Designing Combinatorial Library Mixtures Using a Genetic Algorithm," *Journal of Medicinal Chemistry*, American Chemical Society, vol. 40, No. 15, 1997, pp. 2304–2313.

Gillet, Valerie J. et al., "The Effectiveness of Reactant Pools for Generating Structurally–Diverse Combinatorial Libraries," *Journal of Chemical and Information Computer Sciences*, American Chemical Society, vol. 37, No. 4, 1997, pp. 731–740.

Gillet, Valerie J. et al., "Selecting Combinatorial Libraries to Optimize Diversity and Physical Properties," *Journal of Chemical Information and Computer Sciences*, American Chemical Society, vol. 39, No. 1, 1999, pp. 169–177.

Kearsley, Simon K. et al., "Chemical Similarity Using Physiochemical Property Descriptors," *Journal of Chemical Information and Computer Sciences*, American Chemical Society, vol. 36, No. 1, 1996, pp. 118–127.

Leland, Burton A. et al., "Managing the Combinatorial Explosion," *Journal of Chemical Information and Computer Sciences*, American Chemical Society, vol. 37, No. 1, 1997, pp. 62–70.

Lewis, Richard A. et al., "Similarity Measures for Rational Set Selection and Analysis of Combinatorial Libraries: The Diverse Property–Derived (DPD) Approach," *Journal of Chemical Information and Computer Sciences*, American Chemical Society, vol. 37, No. 3, 1997, pp. 599–614.

Martin, Eric J. and Critchlow, Roger E., "Beyond Mere Diversity: Tailoring Combinatorial Libraries for Drug Discovery," *Journal of Combinatorial Chemistry*, American Chemical Society, vol. 1, No. 1, 1999, pp. 32–45.

Sheridan, Robert P. et al., "Chemical Similarity Using Geometric Atom Pair Descriptors," *Journal of Chemical Information and Computer Sciences*, American Chemical Society, vol. 36, No. 1, 1996, pp. 128–136.

Willett, Peter et al., "Chemical Similarity Searching," *Journal of Chemical Information and Computer Sciences*, American Chemical Society, vol. 38, No. 6, 1998, pp. 983–996.

Agrafiotis, Dimitris K. and Lobanov, Victor S., "Ultrafast Algorithm for Designing Focused Combinational Arrays," *Journal of Chemical Information and Computer Sciences*, American Chemical Society, 2000, vol. 40, No. 4, pp. 1030–1038.

Ajay et al., "Can We Learn To Distinguish between 'Drug–Like' and 'Nondrug–like' Molecules?" *J. Med. Chem.*, 1998, American Chemical Society, vol. 41, No. 18, pp. 3314–3324.

Saunders, M., "Stochastic Exploration of Molecular Mechanics Energy Surfaces. Hunting for the Global Minimum," *Journal of the American Chemical Society*, American Chemical Society, vol. 109, 110, May 13, 1987, pp. 3150–3152.

Brown, Robert D. and Martin, Yvonne C., "The Information Content of 2D and 3D Structural Descriptors Relevant to Ligand–Receptor Binding," *Journal of Chemical Information and Computer Sciences*, American Chemical Society, 1997, vol. 37, No. 1, pp. 1–9.

Brown, Robert D. and Martin, Yvonne C., "Use of Structure–Activity Data To Compare Structure–Based Clustering Methods and Descriptors for Use in Compound Selection," *Journal of Chemical Information and Computer Sciences*, American Chemical Society, 1996, vol. 36, No. 3, pp. 572–584.

Cummins, David J. et al., "Molecular Diversity in Chemical Databases: Comparison of Medicinal Chemistry Knowledge Bases and Databases of Commercially Available Compounds," *Journal of Chemical Information and Computer Sciences*, American Chemical Society, 1996, vol. 36, No. 4, pp. 750–763.

Domine, D. et al., "Non–Linear Mapping for Structure–Activity and Structure–Property Modelling," *Journal of Chemometrics*, John Wiley & Sons, Ltd., vol. 7, No. 4, Jul. –Aug. 1993, pp. 227–242.

Porto, V. et al., "Alternative Neural network Training Methods," *IEEE Expert*, IEEE, vol. 10, No. 4, pp. 16–22.

Downs, Geoff M. and Barnard, John M., "Techniques for Generating Descriptive Fingerprints in Combinatorial Libraries," *Journal of Chemical Information and Computer Sciences*, American Chemical Society, 1997, vol. 37, No. 1, pp. 59–61.

Gillet, Valerie J., "Background Theory of Molecular Diversity," *Molecular Diversity in Drug Design*, Kluwer Academic Publishers, 1999, pp. 43–65.

Good, Andrew C. and Lewis, Richard A., "New Methodology for Profiling Combinatorial Libraries and Screening Sets: Cleaning Up the Design Process with HARPick," *Journal of Medicinal Chemistry*, American Chemical Society, 1997, vol. 40, No. 24, pp. 3926–3936.

Pal, N.R. and Eluri, V.K., "Two Efficient Connectionist Schemes for Structure Preserving Dimensionality Reduction," *IEEE Transactions on Neural Networks*, IEEE, vol. 9, No. 6, Nov. 1998, pp. 1142–1154.

Jamois, Eric A. et al., "Evaluation of Reagent–Based and Product–Based Strategies in the Design of Combinatorial Library Subsets," *Journal of Chemical Information and Computer Sciences*, American Chemical Society, 2000, vol. 40, No. 1, pp. 63–70.

Kim, H. et al., "Self–Organized Distributed Networks for Learning Highly Nonlinear Mapping," *Intelligent Engineering Systems Through Artificial Neural Networks*, American Society of Mechanical Engineers, vol. 4, Nov. 13–16, 1994, pp. 109–114.

Leach, Andrew R. et al., "Implementation of a System for Reagent Selection and Library Enumeration, Profiling, and Design," *Jounal of Chemical Information and Computer Sciences*, American Chemical Society, 1999, vol. 39, No. 6, pp. 1161–1172.

Lobanov, Victor S. and Agrafiotis, Dimitris K., "Stochastic Similarity Selections from Large Combinatorial Libraries," *Journal of Chemical Information and Computer Sciences*, American Chemical Society, Mar./Apr. 2000, vol. 40, No. 2, pp. 460–470.

Matter, Hans and Pötter, Thorsten, "Comparing 3D Pharmacophore Triplets and 2D Fingerprints for Selecting Diverse Compound Subsets," *Journal of Chemical Information and Computer Sciences*, American Chemical Society, 1999, vol. 39, No. 6, pp. 1211–1225.

Matter, Hans, "Selecting Optimally Diverse Compounds from Structure Databases: A Validation Study of Two–Dimensional and Three–Dimensional Molecular Descriptors," *Journal of Medicinal Chemistry*, American Chemical Society, 1997, vol. 40, No. 8, pp. 1219–1229.

Sadowski, Jens and Kubinyi, Hugo, "A Scoring Scheme for Discriminating between Drugs and Nondrugs," *Journal of Medicinal Chemistry*, American Chemical Society, 1998, vol. 41, No. 18, pp. 3325–3329.

Schnur, Dora, "Design and Diversity Analysis of Large Combinatorial Libraries Using Cell–Based Methods," *Journal of Chemical Information and Computer Science*, American Chemical Society, 1999, vol. 39, No. 1, pp. 36–45.

Schuffenhauer, Ansgar et al., "Similarity Searching in Files of Three–Dimensional Chemical Structures: Analysis of the BIOSTER Database using Two–Dimensional Fingerprints and Molecular Field Descriptors," *Journal of Chemical Information and Computer Science*, American Chemical Society, 2000, vol. 40, No. 2, pp. 295–307.

Turner, David B. et al., "Rapid Quantification of Molecular Diversity for Selective Database Acquistion," *Journal of Chemical Information and Computer Science*, American Chemical Society, 1997, vol. 37, No. 1, pp. 18–22.

Wang, Jing and Ramnarayan Kal, "Toward Designing Drug–Like Libraries: A Novel Computational Approach for Prediction of Drug Feasibility of Compounds," *Journal of Combinatorial Chemistry*, American Chemical Society, Nov./Dec. 1999, vol. 1, No. 6, pp. 524–533.

Gasteiger, J. et al, "Assessment of the Diversity of Combinatorial Libraries by an Encoding of Molecular Surface Properties," *Abstracts of Papers Part 1: 211th ACS National Meeting*, Mar. 24–28, 1996, p. 70–CINF.

Hassan, Moises et al., "Optimization and visualization of molecular diversity of combinatorial libraries," *Molecular Diversity*, ESCOM Science Publishers B.V., 1996, vol. 2, pp. 64–74.

Bellman, R.E., *Adaptive Control Processes: A Guided Tour*, Princeton Univ. Press, Princeton, NJ (1961), entire book submitted.

Bezdek, J.C., *Pattern Recognition with Fuzzy Objective Function Algorithms*, Plenum Press, New York, NY (1981), entire book submitted.

Johnson, M.A., and Maggiora, G.M., *Concepts and Applications of Molecular Similarity*, John Wiley and Sons, New York, NY (1990), entire book submitted.

Kohonen, T., *Self–Organizing Maps*, Springer–Verlag, heidelberg, Germany (1995), entire book submitted.

Oja, E., *Subspace Methods of Pattern Recognition*, Research Studies Press Ltd., Letchworth, England (1983), entire book submitted.

Agrafiotis, D.K., "A New Method For Analyzing Protein Sequence Relationships Based On Sammon Maps," *Protein Science*, Cambridge University Press, vol. 6, No. 2, Feb. 1997, pp. 287–293.

Mumenthaler, Ch. And Braun, W., "Automated Assignment of Simulated and Experimental NOESY Spectra of Proteins by Feedback Filtering and Self–correcting Distance Geometry," *Journal of Molecular Biology*, Academic Press Limited, vol. 254, No. 3, Dec. 1, 1995, pp. 465–480.

Amzel, L.M., "Structure–based drug design," *Current Opinion in Biotechnology*, vol. 9, No. 4, Aug. 1998, pp. 366–369.

Blaney, J.M. and Martin, E.J., "Computational approaches for combinatorial library design and molecular diversity analysis," *Current Opinion in Chemical Biology*, Current Biology Ltd., vol. 1, No. 1, Jun. 1997, pp. 54–59.

Meng, E. et al., "Orientational Sampling and Rigid–Body Minimization in Molecular Docking," *Proteins: Structure, Function and Genetics*, Wiley–Liss, Inc., vol. 17, No. 3, 1993, pp. 266–278.

Caflisch, A. and Karplus, M., "Computational combinatorial chemistry for de novo ligand design: Review and assessment," *Perspectives in Drug Discovery and Design*, ESCOM Science Publishers B.V., vol. 3, 1995, pp. 51–84.

Leach, A., "A Survey of Methods for Searching the Conformational Space of Small and Medium–Sized Molecules," *Reviews in Computational Chemistry*, VCH Publishers, vol. 2, pp. 1–55.

Eichler, U. et al., "Addressing the problem of molecular diversity," *Drugs of the Future*, Prous Science, vol. 24, No. 2, 1999, pp. 177–190.

Felder, E.R. and Poppinger, D., "Combinatorial Compound Libraries for Enhanced Drug Discovery Approaches," *Advances in Drug Research*, Academic Press, vol. 30, 1997, pp. 112–199.

Geysen, H.M. and Mason, T.J., "Screening Chemically Synthesized Peptide Libraries for Biologically–Relevant Molecules," *Bioorganic & Medicinal Chemistry Letters*, Pergamon Press Ltd., vol. 3, No. 3, 1993, pp. 397–404.

Gobbi, A. et al., "New Leads By Selective Screening of Compounds From Large Databases," *Abstracts of Papers Part 1: 213th ACS National Meeting*, American Chemical Society, Apr. 13–17, 1997, p. 67–CINF.

Houghten R.A. et al., "The Use of Synthetic Peptide Combinatorial Libraries for the Identification of Bioactive Peptides," *Peptide Research*, vol. 5, No. 6, 1992, pp. 351–358.

Klopman, G., "Artificial Intelligence Approach to Structure––Activity Studies. Computer Automated Structure Evaluation of Biological Activity of Organic Molecules," *Journal of the American Chemical Society*, American Chemical Society, vol. 106, No. 24, 1084, pp. 7315–7321.

Lajiness, M.S. et al., "Implementing Drug Screening Programs Using Molecular Similarity Methods," *QSAR: Quantitative Structure–Activity Relationships in Drug Design*, Alan R. Liss, Inc., 1989, pp. 173–176.

Loew, G.H. et al., "Strategies for Indirect Computer–Aided Drug Design," *Pharmaceutical Research*, Plenum Publishing Corporation, vol. 10, No. 4, 1993, pp. 475–486.

Lynch, M.F. et al., "Genetic Structure Storage and Retrieval," *Journal of Chemical Information and Computer Sciences*, American Chemical Society, vol. 25, No. 3, Aug. 1985, pp. 264–270.

Myers, P.L. et al., "Rapid Reliable Drug Discovery," *Today's Chemist At Work*, American Chemical Society, vol. 6, No. 7, Jul./Aug. 1997, pp. 46–48, 51 & 53.

Pabo, C.O. and Suchanek, E.G., "Computer–Aided Model–Building Strategies for Protein Design," *Biochemistry*, American Chemical Society, vol. 25, No. 20, 1986, pp. 5987–5991.

Saudek, V. et al., "Solution Conformation of Endothelin–1 by H NMR, CD, and Molecular Modeling" *International Journal of Peptide Protein Research*, Munksgaard International Publishers Ltd., vol. 37, No. 3, 1991, pp. 174–179.

Singh, J. et al., "Application of Genetic Algorithms to Combinatorial Synthesis: A Computational Approach to Lead Identification and Lead Optimization," *J. Am. Chem. Soc.*, American Chemical Society, vol. 118, No. 7, Feb. 7, 1996, pp. 1669–1676.

Van Drie, J.H. and Lajiness, M.S., "Approaches to virtual library design," *Drug Discovery today*, Elsevier Science Ltd., vol. 3, No. 6, Jun. 1998, pp. 274–283.

Walters, W.P. et al., "Virtual screening—an overview," *Drug Discovery today*, Elsevier Science Ltd., vol. 3, No. 4, Apr. 1998, pp. 160–178.

Weber, L., "Evolutionary combinatorial chemistry: application of genetic algorithms," *Drug Discovery today*, Elsevier Science Ltd., vol. 3, No. 8, Aug. 1998, pp. 379–385.

Weber, L. et al., "Optimization of the Biological Activity of Combinatorial Compound Libraries by a Genetic Algorithm," *Angewandte Chemie International Edition in English*, VCH, vol. 34, No. 20, Nov. 3, 1995, pp. 2280–2282.

Graybill, T.L. et al., "Enhancing the Drug Discovery Process by Integration of High–Throughput Chemistry and Structure–Based Drug Design," Molecular Diversity and Combinatorial Chemistry: Libraries and Drug Discovery, American Chemical Society, 1996, pp. 16–27.

Saund, E., "Dimensionality–Reduction Using Connectionist Networks," *IEEE Transactions on Pattern Analysis and Machine Intelligence*, IEEE, vol. 11, No. 3, Mar. 1989, pp. 304–314.

"3DP gains drug research patent", *Chemistry in Britain*, The Royal Society of Chemistry, vol. 32, No. 1, Jan. 1996, p. 22.

"Accelerate the Discovery Cycle with Chem–X!", Source and date of publication unclear, 2 pages.

Agrafiotis, D. K., "Stochastic Algorithms for Maximizing Molecular Diversity", *Journal of Chemical Information and Computer Sciences*, American Chemical Society, vol. 37, No. 5, 1997, pp. 841–851.

Alsberg, B.K. et al., "Classification of pyrolysis mass spectra by fuzzy multivariate rule induction–comparison with regression, K–nearest neighbour, neural and decision–tree methods", *Analytica Chimica Acta*, Elsevier Science B.V., vol. 348, No. 1–3, Aug. 20, 1997, pp. 389–407.

Andrea, T.A. and Kalayeh, H., "Applications of Neural Networks in Quantitative Structure–Activity Relationships of Dihydrofolate Reductase Inhibitors", *Journal of Medicinal Chemistry*, American Chemical Society, vol. 34, No. 9, 1991, pp. 2824–2836.

Aoyama, T. et al., "Neural Networks Applied to Quantitative Structure–Activity Relationship Analysis", *Journal of Medicinal Chemistry*, American Chemical Society, vol. 33, No. 9, 1990, pp. 2583–2590.

Aoyama, T. and Ichikawa, H., "Obtaining the Correlation Indices between Drug Activity and Structural Parameters Using a Neural Network", *Chemical & Pharmaceutical Bulletin*, Pharmaceutical Society of Japan, vol. 39, No. 2, Feb. 1991, pp. 372–378.

Kuszewski, J. et al., "Sampling and efficiency of metric matrix distance geometry: A novel partial metrization algorithm," *Journal of Biomolecular NMR*, Escom Science Publishers B.V., vol. 2, No. 1, Jan. 1992, pp. 33–56.

Baum, R.M., "Combinatorial Approaches Provide Fresh Leads for Medicinal Chemisty", *Chemical & Engineering News*, American Chemical Society, Feb. 7, 1994, pp. 20–26.

Bentley, J.L., "Multidimensional Binary Search Trees Used for Associative Searching", *Communications of the ACM*, Association for Computing Machinery, Inc., vol. 18, No. 9, Sep. 1975, pp. 509–517.

Bottou, L. and Vapnik, V. "Local Learning Algorithms", *Neural Computation*, Massachusetts Institute of Technology, vol. 4, No. 6, Nov. 1992, pp. 888–900.

Boulu, L.G. and Crippen, G.M., "Voronoi Binding Site Models: Calculation of Binding Modes and Influence of Drug Binding Data Accuracy", *Journal of Computational Chemistry*, John Wiley & Sons, Inc., vol. 10, No. 5, Jul./Aug. 1989, pp. 673–682.

Boulu, L.G. et al., "Voronoi Binding Site Model of a Polycyclic Aromatic Hydrocarbon Binding Protein", *Journal of Medicinal Chemistry*, American Chemical Society, vol. 33, No. 2, 1990, pp. 771–775.

Cacoullos, T., "Estimation of a Multivariate Density", *Annals of The Institute of Statistical Mathematics*, The Institute of Statistical Mathematics, vol. 18, No. 2, 1966, pp. 179–189.

Clark, R.D., "OptiSim: An Extended Dissimilarity Selection Method for Finding Diverse Representative Subsets", *Journal of Chemical Information and Computer Sciences*, American Chemical Society, vol. 37, No. 6, 1997, pp. 1181–1188.

Clark, D.E., and Westhead, D.R., "Evolutionary algorithms in computer–aided molecular design", *Journal of Computer–Aided Molecular Design*, ESCOM Science Publishers, B.V., vol. 10, No. 4, Aug. 1996, pp. 337–358.

Cramer, III, R. D. et al., "Comparative Molecular Field Analyisis (CoMFA). 1. Effect of Shape on Binding of Steroids to Carrier Proteins", *Journal of The American Society*, American Chemical Society, vol. 110, No. 18, Aug. 31, 1988, pp. 5959–5967.

Cramer, III, R. D. et al., "Substructural Analysis. A Novel Approach to the Problem of Drug Design", *Journal of Medicinal Chemistry*, vol. 17, No. 5, May 1974, pp. 533–535.

Crippen, G. M., "Voronoi Binding Site Models", *Journal of Compoutational Chemistry*, John Wiley & Sons, Inc., vol. 8, No. 7, Oct./Nov. 1987, pp. 1943–955.

Friedman, J. H. et al., "An Algorithm for Finding Best Matches in Logarithmic Expected Time", *ACM Transactions on Mathematical Software*, Association for Computing Machinery, vol. 3, No. 3, Sep. 1977, pp. 209–226.

Friedman, J.H. "Fitting Functions To Noisy Data In High Dimensions", Department of Statistics– Stanford University Technical Report No. 101, (Aug., 1988), pp. 1–36.

Gallop, M. A. et al., "Applications of Combinatorial Technologies to Drug Discovery. 1. Background and Peptide Combinatorial Libraries", *Journal of Medicinal Chemistry*, American Chemical Society, vol. 37, No. 9, Apr. 29, 1994, pp. 1233–1251.

Ghose, A. K. and Crippen, G.M., "Use of Physicochemical Parameters in Distance Geometry and Related Three–Dimensional Quantitative Structure–Activity Relationships: A Demonstration Using *Escherichia coli* Dihydrofolate Reductase Inhibitors", *Journal of Medicinal Chemistry*, American Chemical Society, vol. 28, No. 3, 1985, pp. 333–346.

Good, A. C. et al., "Structure–Activity Relationships from Molecular Similarity Matrices", *Journal of Medicinal Chemistry*, American Chemical Society, vol. 36, No. 4, Feb. 19, 1993, pp. 433–438.

Gordon, E. M. et al., "Applications of Combinatorial Technologies to Drug Discovery. 2. Combinatorial Organic Synthesis, Library Screening Strategies, and Future Directions", *Journal of Medicinal Chemistry*, American Chemical Society, vol. 37, No. 10, May 13, 1994, pp. 1385–1401.

Hartigan, J. A., "Representation of Similarity Matrices By Trees", *Journal of the American Statistical Association*, vol. 62, No. 320, Dec., 1967, pp. 1140–1158.

Hopfinger, A. J., "A QSAR Investigation of Dihydrofolate Reductase Inhibition by Baker Triazines Based upon Molecular Shape Analysis", *Journal of the American Chemical Society*, American Chemical Society, vol. 102, No. 24, Nov. 19, 1980, pp. 7196–7206.

Jackson, R. C., "Update on computer–aidced drug design", *Current Opinion in BIOTECHNOLOGY*, Current Biology Ltd., vol. 6, Dec. 1995, pp. 646–651.

Kim, K. H., "Comparative molecular field analysis (CoMFA)", *Molecular Similarity in Drug Design*, ed. P. M. Dean, Blackie Academic & Professional, 1995, Ch. 12, pp. 291–331.

Kohonen, T., "Self–Organized Formation of Topologically Correct Feature Maps", *Biological Cybernetics*, Springer–Verlag, vol. 43, No. 1, 1982, pp. 59–69.

Koile, K. and Shapiro, R., "Building A Collaborative Drug Design System", *Proceedings of the 25th Hawaii International Conference on System Sciences*, IEEE, 1992, pp. 706–716.

Kowalski, B. R. and Bender, C. F., "Pattern Recognition. II. Linear and Nonlinear Methods for Displaying Chemical Data", *Journal of the American Chemical Society*, American Chemical Society, vol. 95, No. 3, Feb. 7, 1973, pp. 686–693.

Kruskal, J. B., "Nonmetric Multidimensional Scaling: A Numerical Method", *Psychometrika*, vol. 29, No. 2, Jun., 1964, pp. 115–129.

Lengauer, T. and Rarey, M., "Computational methods for biomolecular docking", *Current Opinion in Structural Biology*, Current Biology Ltd, vol. 6, No. 3, Jun., 1996, pp. 402–406.

Luke, B. T., "Evolutionary Programming Applied to the Development of Quantitative Structure–Activity Relationships and Quantitative Structure–Property Relationships", *Journal of Chemical Information and Computer Sciences*, American Chemical Society, vol. 34, No. 6, Nov./Dec. 1994, pp. 1279–1287.

Martin, E. J. et al., "Does Combinatorial Chemistry Obviate Computer–Aided Drug Design?", *Reviews in Computational Chemistry*, VCH Publishers, Inc., vol. 10, 1997, pp. 75–99.

Martin, E. J. et al., "Measuring Diversity: Experimental Design of Combinatorial Libraries for Drug Discovery", *Journal of Medicinal Chemistry*, American Chemical Society, vol. 38, No. 9, Apr. 28, 1995, pp. 1431–1436.

McMartin, C. and Bohacek, R.S., "QXP: Powerful, rapid computer algorithms for structure–based drug design", *Journal of Computer–Aided Molecular Design*, Kluwer Academic Publishers, vol. 11, No. 4, Jul. 1997, pp. 333–344.

Mezey, P. G. and Walker, P.D., "Fuzzy molecular fragments in drug research", *Drug Discovery today*, vol. 2, No. 4, Apr. 1997, pp. 132–137.

Müller, K., "On the paradigm shift from rational to random design", *Journal of Molecular Structure (Theochem)*, Elsevier Science B.V., vol. 398–399, Special Issue, 1997, pp. 467–471.

Jorgensen, W. and Tirado–Rives, J., "Monte Carlo vs. Molecular Dynamics for Conformational Sampling," *Journal of Physical Chemistry*, American Chemical Society, vol. 100, No. 34, Aug. 22, 1996, pp. 14508–14513.

Jain, A. et al., "Artificial Neural Networks: A Tutorial," IEEE, Mar. 1996, pp. 31–44.

Omohundro, S. M., "Bumptrees for Efficient Function, Constraint, and Classification Learning", *Advances in Neural Information Processing Systems 3*, Morgan Kaurmann, 1991, 7 pages, unknown.

Parrill, A.L., "Evolutionary and genetic methods in drug design", *Drug Discovery today*, Elsevier Science Ltd., vol. 1, No. 12, Dec. 1996, pp. 514–521.

Polanski, J., "A neural network for the simulation of biological systems", *Journal of Molecular Structure (Theochem)*, Elsevier Science Ltd., vol. 398–399, Special Issue, 1997, pp. 565–571.

Ramos–Nino, M. E. et al., "A comparison of quantitative structure–activity relationships for the effect of benzoic and cinnamic acids on *Listeria monocytogenes* using multiple linear regression, artificial neural network and fuzzy systems", *Journal of Applied Microbiology*, Society for Applied Bacteriology, vol. 82, No. 2, Feb. 1997, pp. 168–176.

Rogers, D. and Hopfinger, A. J., "Application of Genetic Function Approximation to Quantitative Structure–Activity Relationships and Quantitative Structure–Property Relationships", *Journal of Chemical Information and Computer Sciences*, American Chemical Society, vol. 34, No. 4, Jul./Aug. 1994, pp. 854–866.

Sammon, Jr., J. W., "A Nonlinear Mapping for Data Structure Analysis", *IEEE Transactions on Computers*, IEEE, vol. C–18, No. 5, May 1969, pp. 401–409.

Simon, Z. et al., "Mapping of Dihydrofolate–reductase Receptor Site by Correlation with Minimal Topological (Steric) Differences", *Journal of Theoretical Biology*, Academic Press, Inc., vol. 66, No. 3, Jun. 7, 1997, pp. 485–495.

Smellie, A. S. et al., "Fast Drug–Receptor Mapping by Site–Directed Distances: A Novel Method of Predicting New Pharmacological Leads", *Journal of Chemical Information and Computer Sciences*, American Chemical Society, vol. 31, No. 3, Aug. 1991, pp. 386–392.

Specht, D. F., "A General Regression Neural Network", *IEEE Transactions on Neural Networks*, IEEE, vol. 2, No. 6, Nov. 1991, pp. 568–576.

Svozil, D. et al., "Neural Network Prediction of the Solvatochromic Polarity/Polarizability Parameter $\pi^{H}_{2}$", *Journal of Chemical Information and Computer Sciences*, American Chemical Society, vol. 37, No. 2, 1997, pp. 338–342.

Todorov, N. P. and Dean, P. M., "Evaluation of a method for controlling molecular scaffold diversity in de novo ligand design", *Journal of Computer–Aided Molecular Design*, ESCOM Science Publishers B.V., vol. 11, 1997, pp. 175–192.

Torgerson, W. S., "Multidimensional Scaling: I. Theory and Method", *Psychometrika*, The Psychometric Society, vol. 17, No. 4, Dec. 1952, pp. 401–419.

Vapnik, V., "Principles of Risk Minimization for Learning Theory", *Advances in Neural Information Processing System 4*, Morgan Kaurmann Publishers, Inc., 1992, pp. 831–838.

Vapnik, V. and Bottou, L., "Local Algoithms for Pattern Recognition and Dependencies Estimation", *Neural Computation*, Massachusetts Institute of Technology, vol. 5, No. 6, Nov. 1993, pp. 893–909.

Viswanadhan, V. N. et al., "Mapping the binding site of the nucleoside transporter protein: a 3D–QSAR study", *Biochimica et Biophysica Acta*, Elsevier Science Publishers B.V., vol. 1039, No. 3, 1990, pp. 356–366.

Huang, E. et al., "Distance geometry generates native–like folds for small helical proteins using the consensus distances of predicted protein structures," *Protein Science*, The Protein Society, vol. 7, No. 9, Sep. 1998, pp. 1998–2003.

Westhead, D. R. et al., "A comparison of heuristic search algorithms for molecular docking", *Journal of Computer–Aided Molecular Design*, Kluwer Academic Publishers, vol. 11, 1997, pp. 209–228.

Willett, P., "Genetic algorithms in molecular recognition and design", *Trends in Biotechnology*, Elsevier Science Publishers B.V., vol. 13, No. 12, Dec. 1995, pp. 516–521.

Willett, P. and Winterman, V., "A Comparison of Some Measures for the Determination of Inter–Molecular Structural Similarity Measures of Inter–Molecular Structural Similarity", *Quantitative Structure–Activity Relationships*, VCH, vol. 5, No. 1, Mar. 1986, pp. 18–25.

Zadeh, L. A., "Communicatin Fuzzy Algorithms", *Information and Control*, Academic Press Inc., vol. 12, No. 2, Feb. 1968, pp. 94–102.

Zadeh, L. A., "Fuzzy Sets", *Information and Control*, Academic Press Inc., vol. 8, No. 3, Jun. 1965, pp. 338–353.

Havel, T., "A New Method for Building Protein Conformations from Sequence Alignments with Homologues of Known Structure," *Journal of Molecular Biology*, Academic Press Limited, vol. 217, No. 1, Jan. 5, 1991, pp. 1–7.

Havel, T. and Wüthrich, K., "A Distance Geometry Program for Determining the Structures of Small Proteins and other Macromolecules from Nuclear Magnetic Resonance Measurements of Intramolecular $^1H$–$^1H$ Proximities in Solution," *Bulletin of Mathematical Biology*, Pergamon Press, vol. 46, No. 4, 1984, pp. 673–698.

Aoyama, T. et al., "Neural Networks Applied to Structure–Activity Relationships" *Journal of Medicinal Chemistry*, American Chemical Society, vol. 33., No. 3, 1990, pp. 908–908.

Gasteiger, J. et al., "Analysis of the Reactivity of Single Bonds in Aliphatic Molecules by Statistical and Pattern Recognition Methods," *Journal of Chemical Information and Computer Sciences*, American Chemical Society, vol. 33, No. 3, 1993, pp. 385–394.

Guez, A. and Nevo, I., "Neural networks and fuzzy logic in clinical laboratory computing with application to integrated monitoring," *Clinica Chimica Acta*, Elsevier Science Publishers B.V., vol. 248, 1996, pp. 73–90.

Rouvray, D.H., "Similarity in Chemistry: Past, Present and Future," *Topics in Chemistry*, Springer–Verlag, vol. 173, 1995, pp. 1–30.

de Ridder, D. and Duin, R.P.W., "Sammon's mapping using neural networks: A comparison," *Pattern Recognition Letters*, Elsevier Science Publishers B.V., vol. 18, No. 11–13, 1997, pp. 1307–1316.

Havel, T. and Wüthrich, K., "An Evaluation of the Combined Use of Nuclear Magnetic Resonance and Distance Geometry for the Determination of Protein Conformations in Solution," *Journal of Molecular Biology*, Academic Press Inc., vol. 182, No. 2, Mar. 20, 1985, pp. 281–294.

Chang, G. et al., An Internal Coordinate Monte Carlo Method for Searching Conformational Space, *Journal of the American Chemical Society*, American Chemical Society, vol. III, Jun. 1689, No. 12, pp. 4379–4386.

Crippen, G.M. and Havel, T.F., *Distance Geometry and Molecular Conformation*, Research Studies Press Ltd., 1988, entire book submitted.

Feuston, B. et al., "Comparison of Knowledge–Based and Distance Geometry Approaches for Generation of Molecular Conformations," *Journal of Information and Computer Sciences*, American Chemical Society, vol. 41, No. 3, 2001, pp. 754–763.

Ferguson, D. and Raber, D., "A New Approach to Probing Conformational Space with Molecular Mechanics: Random Incremental Pulse Search," *Journal of the American Chemical Society*, American Chemical Society, vol. 111, No. 12, 1989, pp. 4371–4378.

Halgren, T. and Nachbar, R., "Merck Molecular Force Field. IV. Conformational Energies and Geometries for MMFF94*," *Journal of Computational Chemistry*, John Wiley & Sons, Inc., vol. 17, Nos. 5 & 6, 1996, pp. 587–915.

Halgren, T., "Merck Molecular Force Field. V. Extension of MMFF94 Using Experimental Data, Additional Computational Data, and Empirical Rules*," *Journal of Computational Chemistry*, John Wiley & Sons, Inc., vol. 17, Nos. 5 & 6, Apr. 1996, pp. 616–641.

* cited by examiner

```
PROC REDUCTIVE_AMINATION {LIBRARY AMINES ALDEHYDES}
{
    DEFINE REAGENT AMINE AS "[C,c][NH2]" OR "C[NH]C" AND NOT
"C(=O)[NH,NH2]";
    DEFINE REAGENT ALDEHYDE AS "C[CH]=O";
    DEFINE PRODUCT p;
    p ADD AMINE FROM $AMINES;
    p ADD ALDEHYDE FROM $ALDEHYDES;
    p INSERT BOND ALDEHYDE:1 AMINE:1;
    p REMOVE ATOM ALDEHYDE:2;
    ENUMERATE p AS $LIBRARY;
}
```

FIG. 8

```
<PRODUCT> ADD <REAGENT> FROM <SOURCE>
<PRODUCT> INSERT BOND <r1:a1> <r2:a2> [<ORDER>] [<STEREO>]
<PRODUCT> REMOVE ATOM <r1:a1>
<PRODUCT> REMOVE BOND <r1:a1> <r1:a2>
<PRODUCT> REMOVE ATTACHMENT <r1:a1>
<PRODUCT> REMOVE FRAGMENT <r1:a1> <r1:a2>
<PRODUCT> SET ATOM <r1:a1> CHARGE|RADICAL <VALUE>
<PRODUCT> SET BOND <r1:a1> <r1:a2> <ORDER> [<STEREO>]
<PRODUCT> SET ATOM <r1:a1> CONFIGURATION <r1:a2> <r1:a3>
<r1:a4> <r1:a5> UP|DOWN
```

FIG. 9

```
PROC CYCLO_ADDITION {LIB OLEFINS BROMINATING_AGENTS} {
    DEFINE REAGENT OLEFIN AS "C=C";
    DEFINE REAGENT BRAGENT AS "C([Br])([Br])[Br]";
    DEFINE PRODUCT p;
    p ADD OLEFIN FROM $OLEFINS;
    p ADD BRAGENT FROM $BROMINATING_AGENTS;
    p INSERT BOND OLEFIN:0 BRAGENT:0;
    p INSERT BOND OLEFIN:1 BRAGENT:0;
    p REMOVE ATOM BRAGNET:3;
    p SET BOND OLEFIN:0 OLEFIN:1 SINGLE SYN_PRODUCT;
    ENUMERATE p AS $LIB;
};
```

FIG. 10

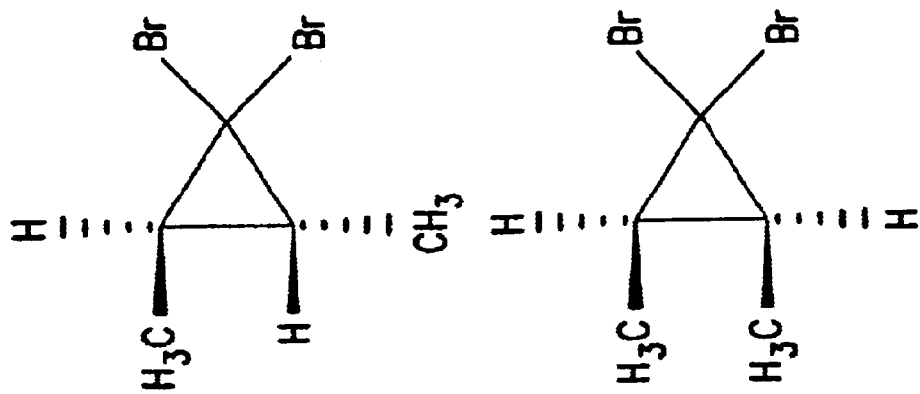
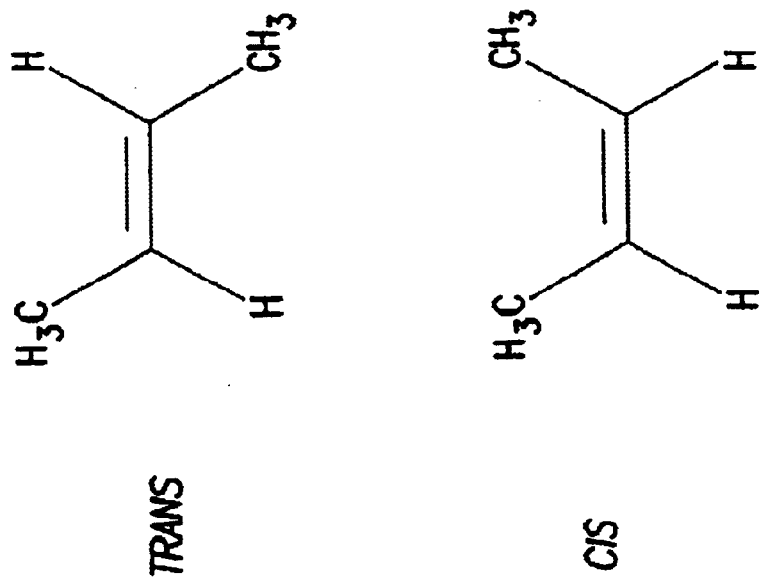
FIG. 11

```
PROC ANTI_ELIMINATION {LIB r1s} {
    DEFINE REAGENT r1 AS "[CH]C[Br]";
    DEFINE PRODUCT p;
    p ADD r1 FROM $r1s;
    p REMOVE ATOM r1:2;
    p SET BOND r1:0 r1:1 DOUBLE ANTI_PRODUCT;
    ENUMERATE p AS $LIB;
};
```

FIG. 12

```
PROC SN_INVERSION {LIB r1s r2s} {
   DEFINE r1 AS "[C&X4]O";
   DEFINE r2 AS "C(=O)O";
   DEFINE PRODUCT p;
   p ADD r1 FROM $r1s;
   p ADD r2 FROM $r2s;
   p REMOVE FRAGMENT r1:0 r1:1;
   p INSERT BOND r1:0 r2:2 SINGLE;
   p SET ATOM r1:0 CONFIGURATION INVERSE;
   ENUMERATE p AS $LIB;
};
```

FIG. 14

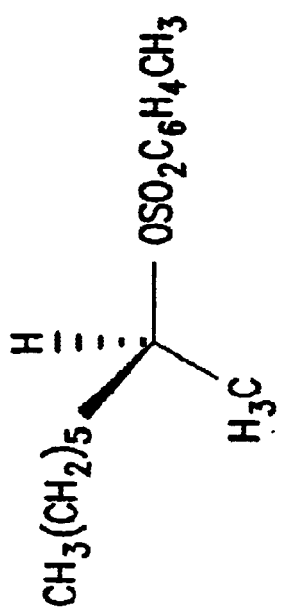
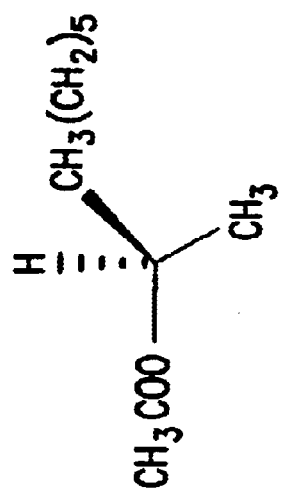
FIG. 15

```
PROC DIELS_ALDER {LIB r1s r2s} {
    DEFINE REAGENT DIENE AS "C1C=CC=C1";
    DEFINE REAGENT DIENOPHILE AS "*C=C*";
    DEFINE PRODUCT p;
    p ADD DIENE FROM $r1s;
    p ADD DIENOPHILE FROM $r2s;
    p INSERT BOND DIENE:1 DIENOPHILE:1;
    p INSERT BOND DIENE:4 DIENOPHILE:2;
    p SET BOND DIENE:1 DIENE:2 SINGLE;
    p SET BOND DIENE:3 DIENE:4 SINGLE;
    p SET BOND DIENE:2 DIENE:3 DOUBLE;
    p SET BOND DIENOPHILE:1 DIENOPHILE:2 SINGLE;
    p SET ATOM DIENOPHILE:1 CONFIGURATION DIENOPHILE:2 DIENOPHILE:0 DIENOPHILE:2 DIENE:1 H UP;
    p SET ATOM DIENOPHILE:2 CONFIGURATION DIENOPHILE:1 DIENOPHILE:4 DIENOPHILE:0 DIENOPHILE:1 DIENE:3 H UP;
    p SET ATOM DIENE:1 CONFIGURATION DIENE:2 DIENE:0 DIENOPHILE:1 H DOWN;
    p SET ATOM DIENE:4 CONFIGURATION DIENE:2 DIENE:0 DIENOPHILE:2 DIENE:3 H DOWN;
    ENUMERATE LIBRARY AS SUB;
};
```

FIG. 16

METHOD, SYSTEM, AND COMPUTER PROGRAM PRODUCT FOR ENCODING AND BUILDING PRODUCTS OF A VIRTUAL COMBINATORIAL LIBRARY

CROSS-REFERENCE TO RELATED APPLICATIONS

This application claims the benefit of U.S. Provisional Application No. 60/234,206, filed Sep. 20, 2000, which is incorporated by reference herein in its entirety.

FIELD OF THE INVENTION

The present invention relates to combinatorial chemistry. More particularly, it relates to virtual combinatorial libraries used in computer aided molecular design.

BACKGROUND OF THE INVENTION

Among the tools available to a medicinal chemist, combinatorial chemistry is one of the most powerful and best suited for exploring chemical space in search of new drug leads. Combinatorial chemistry provides access to millions of novel compounds from a limited number of building blocks using synthetic procedures that work reliably across a wide range of starting materials.

A virtual combinatorial library is a collection of chemical compounds or products, in electronic form, generated by combining a number of chemical building blocks such as reagents. For example, a polypeptide virtual combinatorial library can be formed by combining a set of chemical building blocks called amino acids, in electronic form, in every possible or nearly every possible way for a given compound length (i.e., the number of amino acids in a polypeptide compound).

Generally speaking, there are two kinds of virtual combinatorial libraries that can be formed: a viable library and an accessible library. A viable library is relatively small in size. It is assembled from readily available reagents that have been filtered, for example, by a medicinal chemist. A viable library will often have a physical counterpart. An accessible library, on the other hand, is relatively large in size. It can encompass millions or billions of products. An accessible library will typically include all possible reagents that are in principle compatible with a particular chemical reaction scheme. Typically, an accessible library is so large that it can never be physically synthesized in its entirety. Thus, in many cases, appropriate selection techniques must be applied to an accessible library in order to identify a subset of compounds or products for physical synthesis and biological testing. In order to take advantage of robotic hardware, minimize the number of reagents, and simplify the logistical aspects of a chemical experiment, physical libraries are almost invariably synthesized in the form of arrays, which represent the products derived by combining a given subset of reagents in all possible combinations as prescribed by the reaction scheme.

Depending on their use, virtual combinatorial libraries are divided into two main categories: (1) focused or directed libraries, which are biased against a specific target, structural class, or known pharmacophore; and (2) exploratory or probe libraries, which are target-independent and are designed to span a wide range of physicochemical and structural characteristics. Focused libraries are typically designed to follow up on a known lead, optimize a set of properties, or validate some structure-activity hypothesis. Access to the chemical structures of the products is required in order to assess molecular similarity, predict biological activity, or estimate some other property of interest. In contrast, probe libraries explore chemical space in search of novel hits, and their design is based predominantly on molecular diversity. Although fairly diverse libraries can be built by selecting a diverse set of reagents, there is overwhelming evidence (see V. J. Gillet et al., The effectiveness of reactant pools for generating structurally-diverse combinatorial libraries, *J. Chem. Inf. Comput. Sci.*, 1997, 37, 731-740; and E. A. Jamois et al., Evaluation of reagent-based and product-based strategies in the design of combinatorial library subsets, *J. Chem. Inf. Comput. Sci.*, 2000, 40, 63-70, which is incorporated by reference herein in its entirety), but not conclusive evidence (see A. Linusson et al., Statistical Molecular Design of Building Blocks for Combinatorial Chemistry, *J. Med. Chem.*, 2000, 43, 1320-1328; and E. J. Martin et al., Oriented Substituent Pharmacophore PropErtY Space (OSPPREYS): A substituent-based calculation that describes combinatorial library products better than the corresponding product-based calculation, *J. Mol. Graphics Modell.*, 2000, 18, 383-403, each of which is incorporated by reference herein in its entirety), which suggests that product-based designs are substantially better.

Experience suggests that selections based exclusively on molecular diversity tend to include "extreme" reagents, which can increase cost, cause delays due to limited availability, lead to unforeseen synthetic problems, and produce unusual compounds of limited pharmaceutical interest. The hit rate achieved with such libraries has proven disappointingly low (see A. R. Leach and M. M. Hann, The in silico world of virtual libraries, *Drug Discovery Today*, 2000, 5, 326-336, each of which is incorporated by reference herein in its entirety), and the compounds often exhibit unfavorable biological properties that could potentially result in ADME liabilities (see C. A. Lipinski et al., Experimental and computational approaches to estimate solubility and permeability in drug discovery and development settings. *Adv. Drug Deliv. Rev.* 1997, 23, 3-25; and D. N. Rassokhin and D. K. Agrafiotis, Kolmogorov-Smirnov statistic and its application in library design, *J. Mol. Graphics Modell.*, 2000, 18(4-5), 370-384, each of which is incorporated by reference herein in its entirety). Thus, the focus in the design of probe libraries has began to shift from pure diversity to chemical feasibility, availability of monomers, and drug likeness (see D. N. Rassokhin and D. K. Agrafiotis, Kolmogorov-Smirnov statistic and its application in library design, *J. Mol. Graphics Modell.*, 2000, 18(4-5), 370-384; A. R. Leach and M. M. Hann, The in silico world of virtual libraries, *Drug Discovery Today*, 2000, 5, 326-336; J. Sadowski and H. Kubinyi, A scoring scheme for distinguishing between drugs and non-drugs. *J. Med. Chem.*, 1998, 41, 3325-3329; Ajay et al., Can we learn to distinguish between "drug-like" and "nondrug-like" molecules?, *J. Med. Chem.*, 1998, 41, 3314-3324; and J. Wang and K. Ramnarayan, Toward designing drug-like libraries: a novel computational approach for prediction of drug feasibility of compounds, *J. Comb. Chem.*, 1999, 1, 524-533, each of which is incorporated by reference herein in its entirety).

Creating designs that combine molecular diversity or similarity with desired property profiles and drug likeness requires the use of optimization techniques such as simulated annealing (see D. K. Agrafiotis, Stochastic algorithms for maximizing molecular diversity, *J. Chem. Inf. Comput. Sci.*, 1997, 37, 841-851; D. K. Agrafiotis, On the use of information theory for assessing molecular diversity. *J. Chem. Inf. Comput. Sci.*, 1997, 37(3), 576-580; D. K. Agrafiotis and V. S. Lobanov, An efficient implementation of distance-based diversity metrics based on k-d trees, *J. Chem. Inf. Comput. Sci.*, 1999, 39(1), 51–58; M. Hassan et al., Optimization and visualization of molecular diversity of combinatorial libraries, *J. Comput. Aided. Mol. Des.*, 1996, 2, 64–74; and A. C. Good and R. A. Lewis, New methodology for profiling combinatorial libraries and screening sets: cleaning up the design process with HARPick, *J. Med. Chem.*, 1997, 40, 3926–3936, each of which is incorporated by reference herein in its entirety) or genetic algorithms (see U.S. Pat. Nos. 5,463,564; 5,574,656; 5,684,711; and 5,901,069 to D. K. Agrafiotis et al.; R. D. Brown and Y. C. Martin, Designing combinatorial library mixtures using a genetic algorithm, *J. Med. Chem.*, 1997, 40, 2304–2313; and V. J. Gillet et al., Selecting combinatorial libraries to optimize diversity and physical properties, *J. Chem. Inf. Comput. Sci.*, 1999, 39, 169–177, each of which is incorporated by reference herein in its entirety) and access to the properties of the individual products. To that end, in silico enumeration or virtual library generation becomes an essential part of the design process.

Despite advances in the processing speed and storage capacity of modern computers, there are many combinatorial libraries that defy enumeration. Enumeration, or product expansion, refers to the translation of a library into a database containing connection tables for the products of the library. For example, it is easy to imagine a combinatorial library containing $10^{12}$ compounds (see R. D. Cramer et al., Virtual compound libraries: a new approach to decision making in molecular discovery research. *J. Chem. Inf. Comput. Sci.* 1998, 38, 1010–1023, which is incorporated by reference herein in its entirety), which would require over three years to enumerate at a rate of 10,000 structures per second. Since most of the descriptors that are typically employed in diversity profiling, similarity searching and QSAR are calculated at a much slower rate, an exhaustive analysis of such a library would be impossible. Hence, there is a need for virtual library enumeration and analysis techniques that are scalable and that can be applied to massive virtual libraries containing hundreds of millions of compounds.

SUMMARY OF THE INVENTION

The present invention provides a method, system, and computer program product for encoding and building products of a virtual combinatorial library. As described herein, the invention involves a pre-calculation or encoding stage in which data and computer instructions needed to build products of a virtual combinatorial library are generated, compiled, and stored in a compact data structure for subsequent retrieval. This stage of the invention eliminates any need to fully enumerate the virtual combinatorial library whenever a product is needed. The invention also involves a real-time or building stage, in which the data and computer instruction of the stored data structure are accessed and used, for example, to quickly build or generate product connection tables for selected product of the library on an as needed basis.

As described herein, during the encoding stage of embodiments of the invention at least one chemical transformation for generating product connection data from reagent connection data and one or more reagent substructure patterns involved in forming the products of the virtual combinatorial library are encoded in a computer readable form (e.g., a scripting language). A compiler operates on the encoded information and generates reagent mapping data. The reagent mapping data is generated from the one or more reagent substructure patterns and reagent connection data for a set of reagents from which the products of the virtual combinatorial library are formed. In an embodiment, the reagent mapping data encodes how an atom or group of atoms of the one or more reagent substructure patterns is mapped to an atom or group of atoms of a reagent molecule. The compiler compiles the encoded at least one chemical transformation to generate computer instructions that can control the operation of a processor. A library object containing the compiled computer instructions, the generated reagent mapping data, and the reagent connection data for the set of reagents is then generated and stored in a memory.

During the building stage of embodiments of the invention, a builder is used to generate product connection data for the products of the virtual combinatorial library. The builder uses the compiled computer instructions stored as a part of the library object. The builder operates on reagent mapping data and reagent connection data retrieved from the library object. In an embodiment, the reagent mapping data is stored as a plurality of reaction maps, and the reagent connection data for the set of reagents is stored as a plurality of reagent connection tables. In an embodiment, the output of the builder is a product connection table for each product built.

In an embodiment, data needed to build a particular product is retrieved using a product identification number. In another embodiment, data needed to build a particular product is retrieved using an identification number associated with one or more reagents used to form the particular product.

Further embodiments, features, and advantages of the present invention, as well as the structure and operation of the various embodiments of the present invention, are described in detail below with reference to the accompanying figures.

BRIEF DESCRIPTION OF THE DRAWINGS/FIGURES

The present invention is described with reference to the accompanying drawings wherein.

Figure 3A:
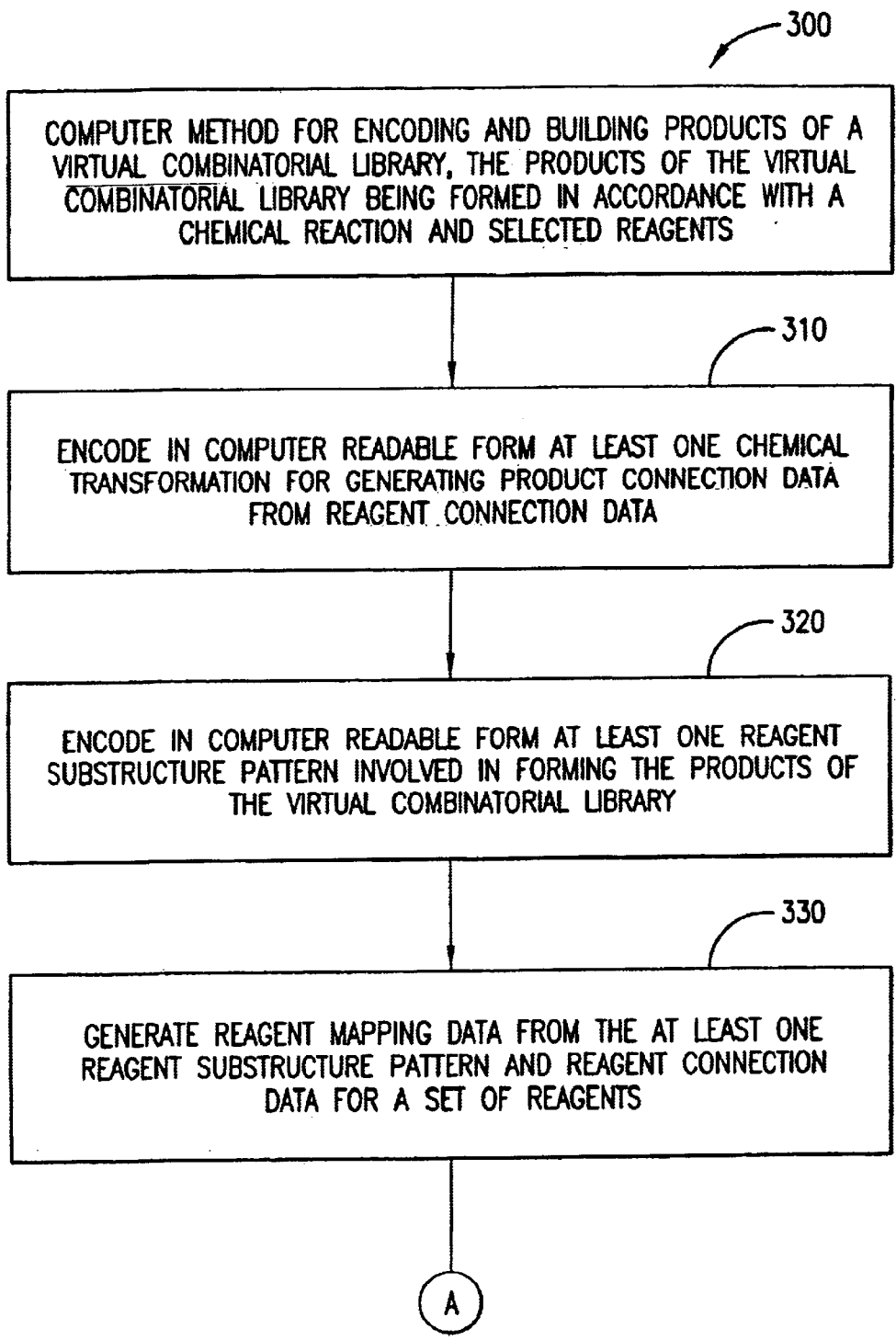
Figure 3B:
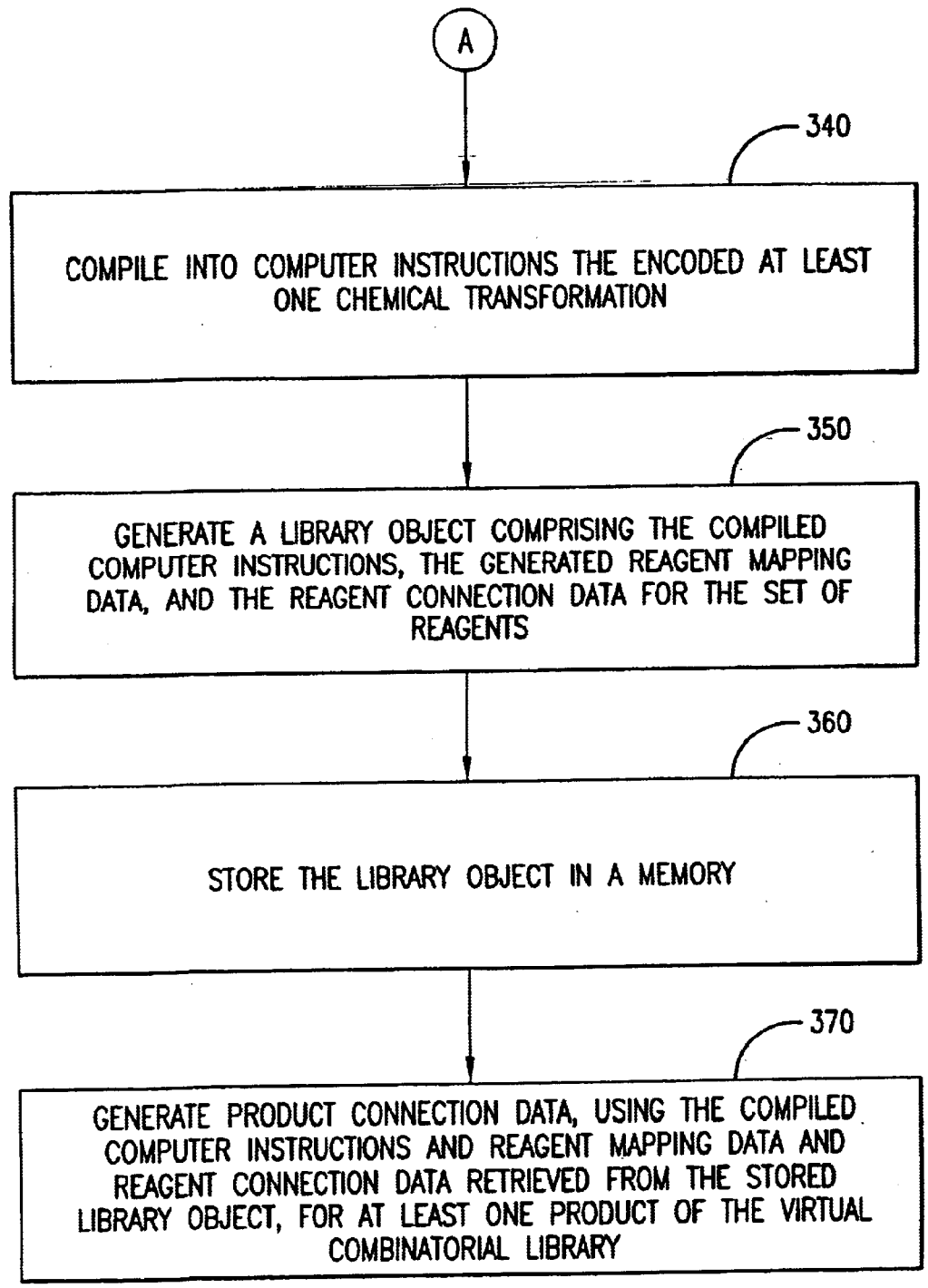
Figure 4:
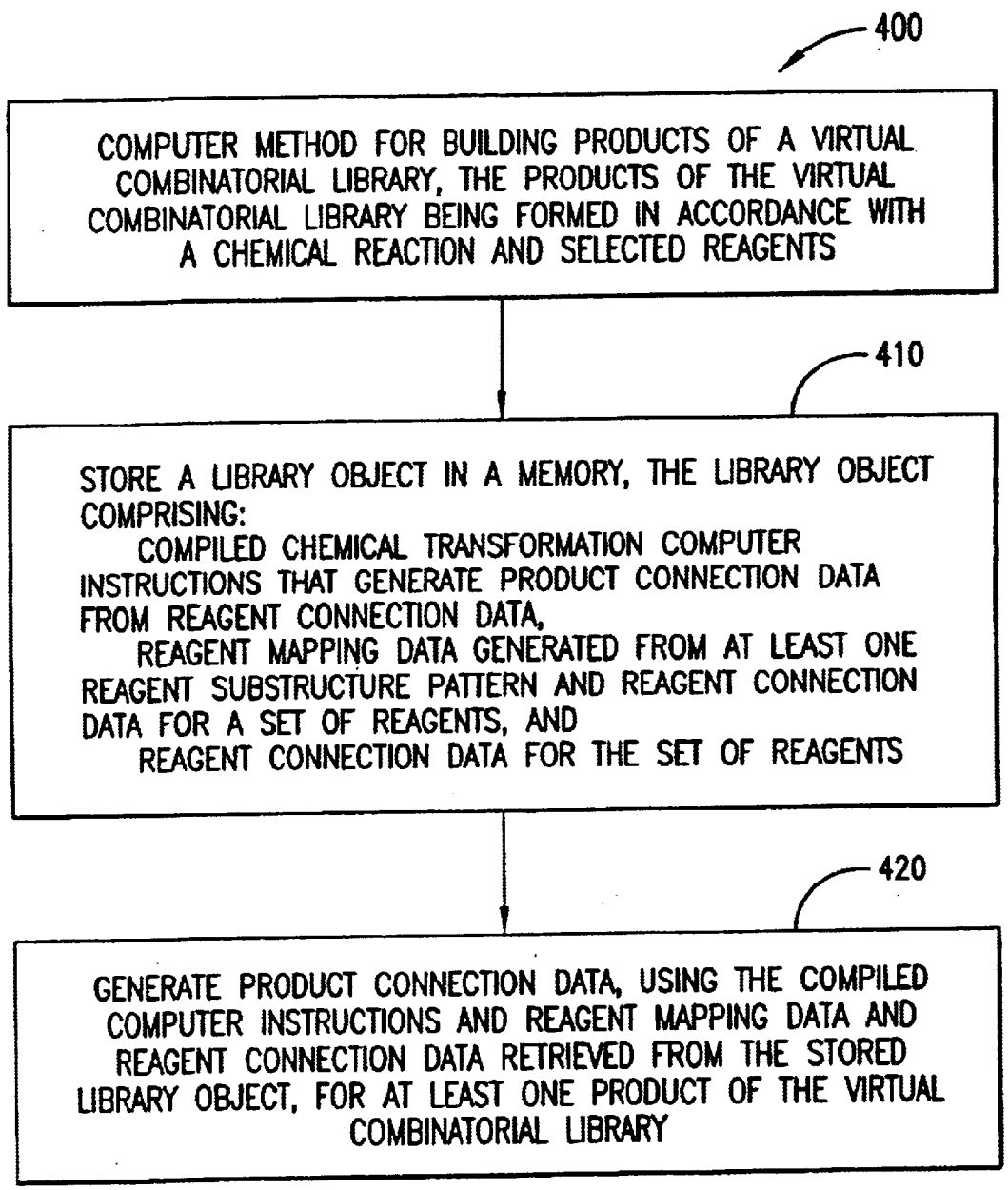
Figure 5:
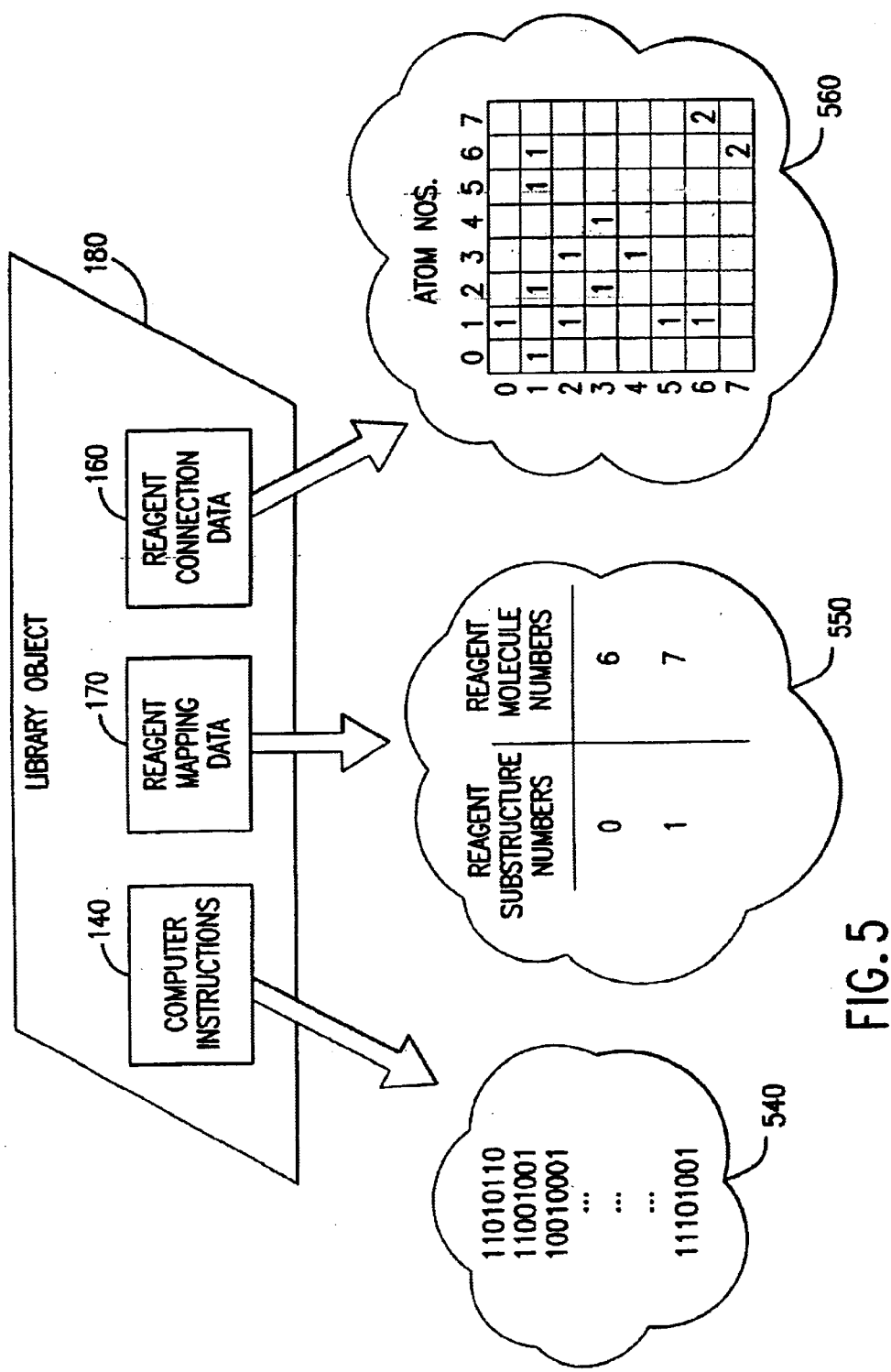
Figure 6:
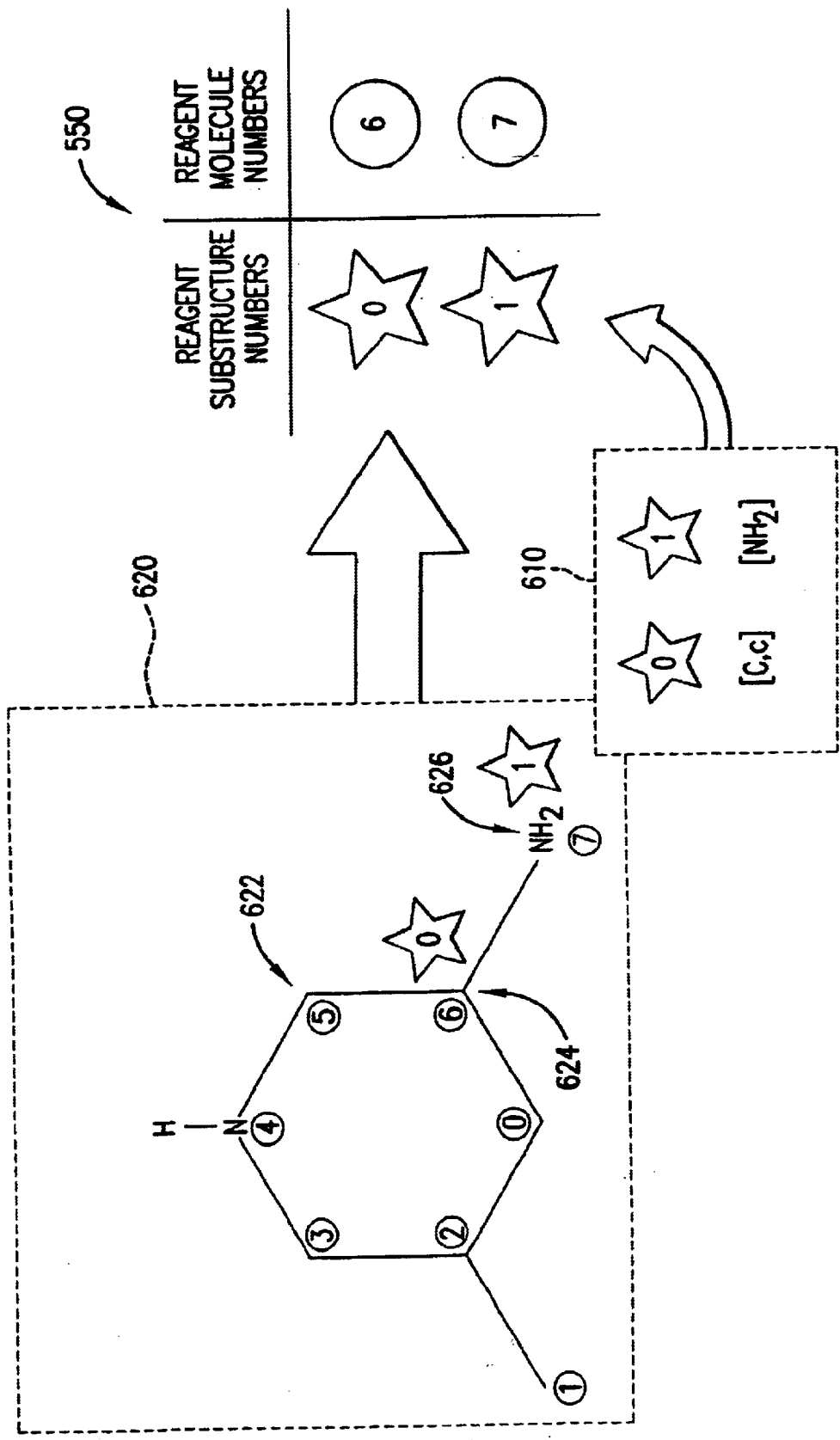
Figure 7:
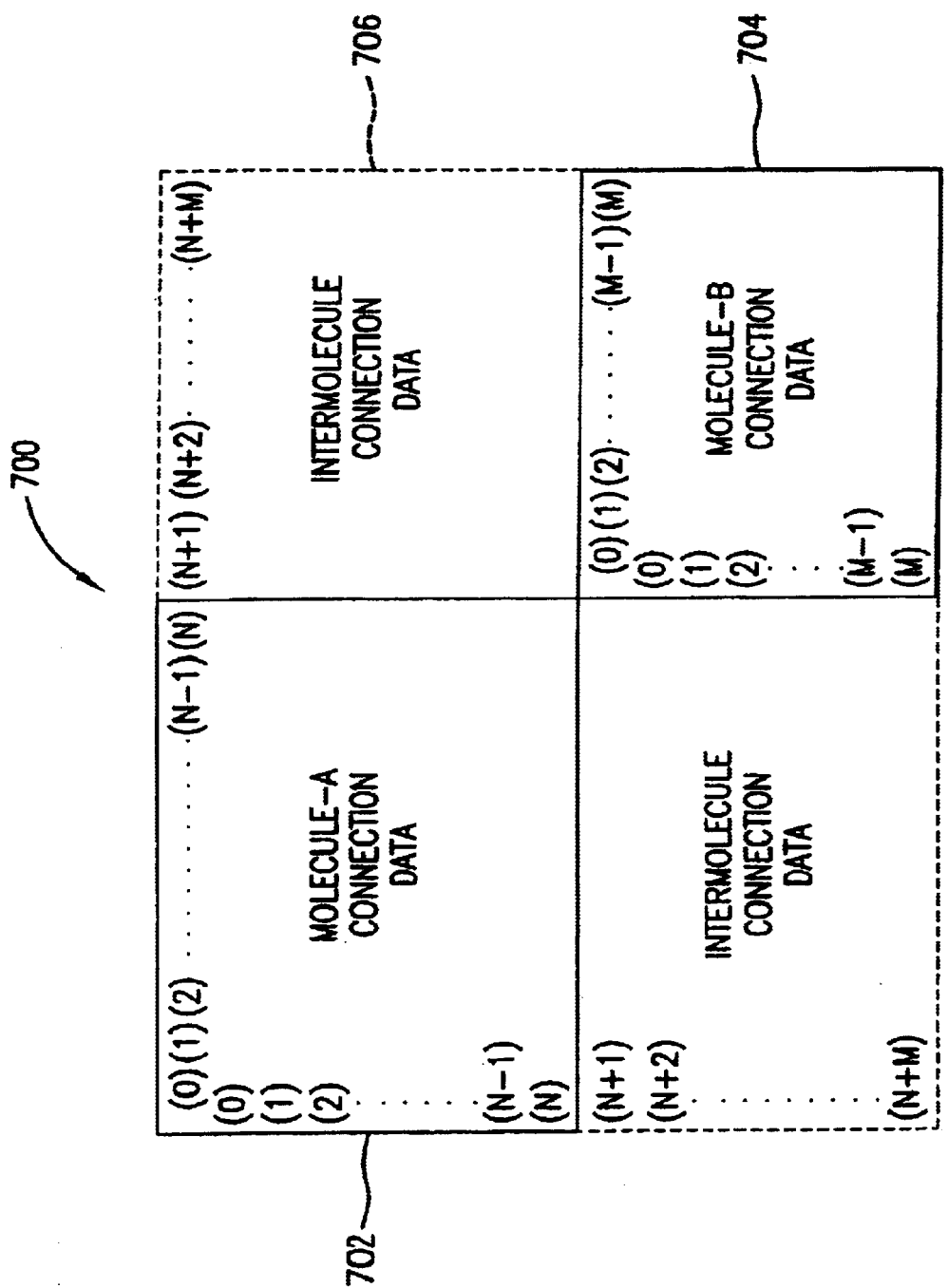
Figure 13:
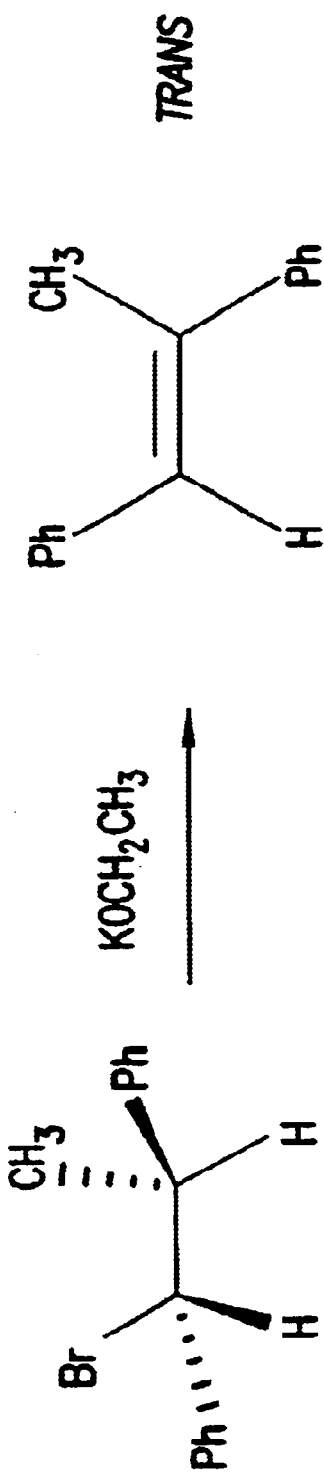
Figure 17:
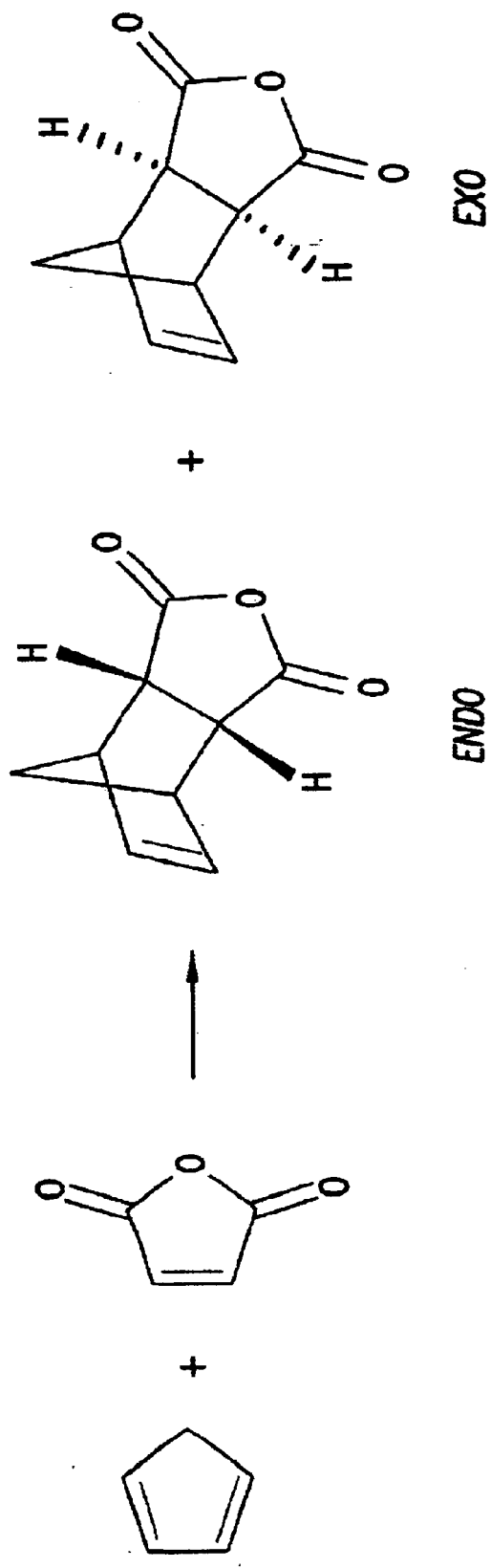

FIGS. 3A–B illustrate a flowchart of a method for encoding and building products of a virtual combinatorial library according to an embodiment of the invention;

FIG. 4 illustrates a flowchart of a method for building products of a virtual combinatorial library according to an embodiment of the invention;

FIG. 5 illustrates a library object according to an embodiment of the invention;

FIG. 6 illustrates how a reaction map is generated according to an embodiment of the invention;

FIG. 7 illustrates an example product connection table according to an embodiment of the invention;

FIG. 8 illustrates example script for generating a virtual combinatorial library based on the reductive amination reaction according to an embodiment of the invention;

FIG. 9 illustrates frequently used operators (instructions) according to an embodiment of the invention;

FIG. 10 illustrates an example encoding of a stereochemical reaction according to an embodiment of the invention;

FIG. 11 illustrates the encoded reaction of FIG. 10;

FIG. 12 illustrates an example encoding of a stereochemical reaction according to an embodiment of the invention;

FIG. 13 illustrates the encoded reaction of FIG. 12;

FIG. 14 illustrates an example encoding of a stereochemical reaction according to an embodiment of the invention;

FIG. 15 illustrates the encoded reaction of FIG. 14;

FIG. 16 illustrates an example encoding of a stereochemical reaction according to an embodiment of the invention;

FIG. 17 illustrates the encoded reaction of FIG. 16; and

Figure 18:
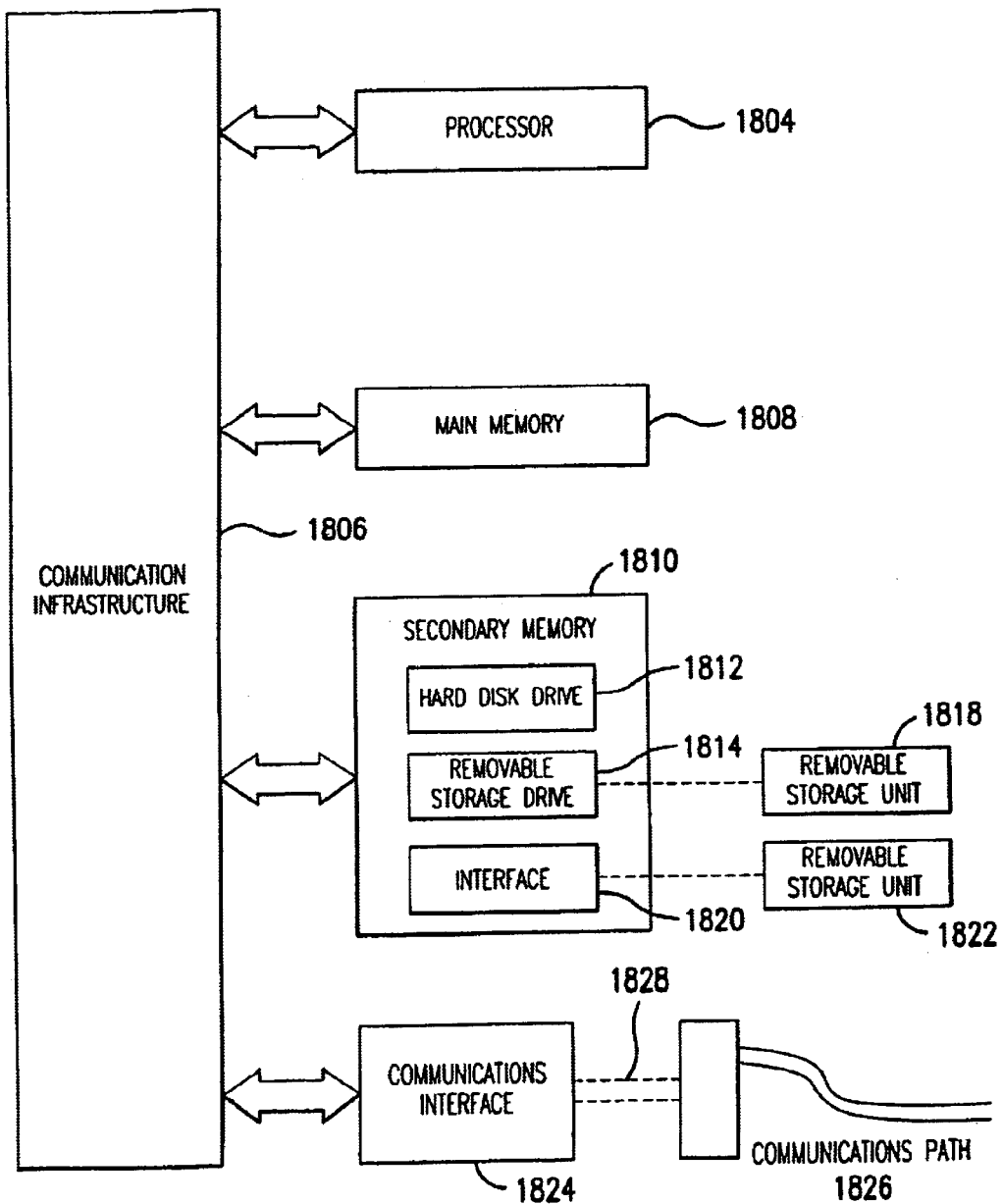

FIG. 18 illustrates an exemplary computing environment according to an embodiment of the invention.

DETAILED DESCRIPTION OF THE INVENTION

Embodiments of the present invention are now described with references to the figures, where like reference numbers indicate identical or functionally similar elements. Also in the figures, the left most digit(s) of each reference number corresponds to the figure in which the reference number is first used. While specific configurations and arrangements are discussed, it should be understood that this is done for illustrative purposes only. One skilled in the relevant art will recognize that other configurations and arrangements can be used without departing from the spirit and scope of the invention. It will also be apparent to one skilled in the relevant art(s) that this invention can also be employed in a variety of other devices and applications.

Overview of the Invention

The present invention provides a method, system, and computer program product for encoding and building products of a virtual combinatorial library. As described herein, the invention involves a pre-calculation or encoding stage in which data and computer instructions needed to build products of a virtual combinatorial library are generated, compiled, and stored in a compact data structure for subsequent retrieval. This stage of the invention eliminates any need to fully enumerate the virtual combinatorial library whenever a product is needed. The invention also involves a real-time or building stage, in which the data and computer instruction of the stored data structure are accessed and used, for example, to quickly build or generate product connection tables for selected product of the library on an as needed basis.

In operation during the encoding stage, at least one chemical transformation for generating product connection data from reagent connection data and reagent substructure patterns involved in forming the products of the virtual combinatorial library are encoded in a computer readable form (e.g., a scripting language). A compiler then operates on the encoded information and generates reagent mapping data. In an embodiment, the reagent mapping data encodes how an atom or group of atoms of the reagent substructure patterns are mapped to an atom or group of atoms of a reagent molecule. The compiler also compiles the encoded chemical transformation to generate computer instructions that can control the operation of a processor. A data structure, referred to herein as a library object, is then generated. This library object can be stored in a memory (e.g., on a computer disk) and used at a later time to build any or all of the products of the virtual combinatorial library. In an embodiment, the library object includes compiled computer instructions, reagent mapping data, and reagent connection data.

As described herein, during the building stage of the invention, a library object according to the invention can be used to gain immediate access to any of the products of the virtual combinatorial library. In an embodiment, a builder according to the invention uses the compiled computer instructions of a library object, and operates on reagent mapping data and reagent connection data retrieved from the library object to generate products or product connection data. In an embodiment, the output of the builder is a product connection table for each product built.

Embodiments of the Invention

FIGS. 1–4 illustrate embodiments of the invention for encoding and/or building products of a virtual combinatorial library.

Figure 1:
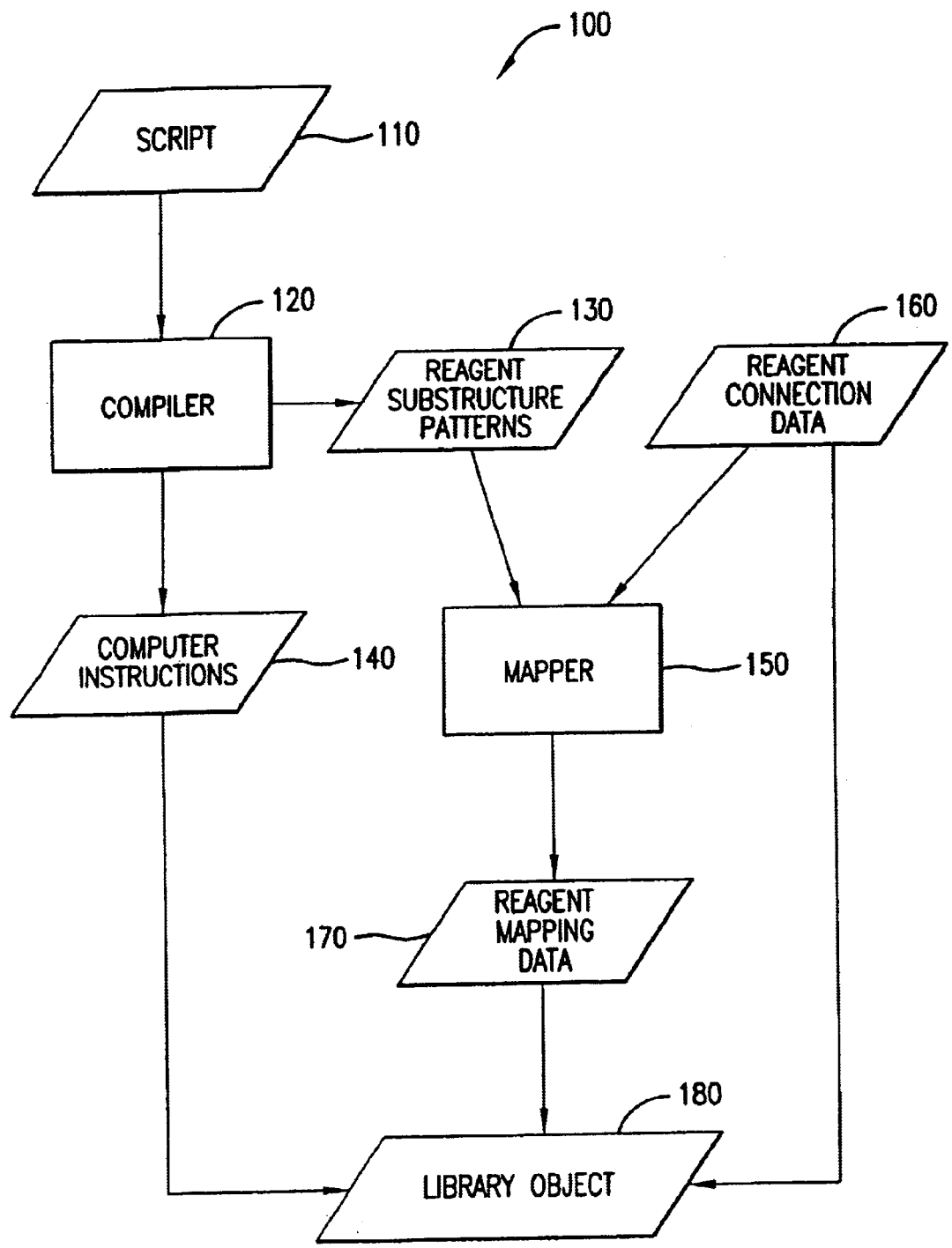
FIG. 1 illustrates a flowchart of an embodiment of the invention for encoding products of a virtual combinatorial library.

FIG. 1 illustrates a flowchart of an embodiment 100 for encoding the products of a virtual combinatorial library in a compact data structure or library object 180 according to the invention. As described herein, embodiment 100 facilitates fast, "on-demand" enumeration or building of combinatorial products. As described in detail below, method 100 comprises three operation stages or steps. A person skilled in the relevant art will understand how to implement embodiment 100 based on the description of the invention herein.

Prior to step one of method 100, a chemical reaction or chemical transformation used to combine reagents and form products is encoded in a computer readable form or script 110. In an embodiment, a reaction scripting language (RSL) or scripting language is used to facilitate the encoding of chemical transformations. An RSL according to an embodiment of the invention is described below in the Library Construction section. Advantages of using an RSL according to the invention include versatility, speed, and scalability.

In stage or step one of embodiment 100, a compiler 120 is used to operate on script 110 and generate reagent substructure patterns 130. FIG. 6 illustrates an example reagent substructure pattern 610. In an embodiment, SMARTS notation (see C. A. James et al., Daylight Theory Manual Daylight 4.71, Daylight Chemical Information Systems, Inc., 2000, http://www.daylight.com/dayhtml/doc/theory/theory.toc.html, which is incorporated by reference herein in its entirety) is used to encode the reagent substructural patterns 130 that are involved in the encoded chemical transformations and that must be present in order for reagents selected from a set of reagents to undergo a reaction. Each reagent can be defined using multiple patterns. The order in which the multiple patterns are defined in script 110 specifies the relative reactivity of the respective functional groups. For example, for the amination library of FIG. 8, lines 5 and 6 specify that both primary and secondary amines can react with an aldehyde. This feature of the invention is further described below in the Library Construction section.

In stage or step one of embodiment 100, compiler 120 is also used to operate on script 110 and generate computer instructions 140. As described in more below in the Library construction section and elsewhere herein, computer instructions 140 are compiled computer instructions or computer logic for controlling the operation of a processor. FIG. 5 shows illustrative compiled computer instructions 540. Computer instructions 140 are used to control a processor and thereby generate product connection data from reagent connection data and reagent mapping data (e.g., reaction maps) according to the invention. As illustrated in FIG. 5, computer instructions 140 form a part of library object 180.

In stage or step two of embodiment 100, a mapper 150 operates on reagent substructure patterns 130 and reagent connection data 160 to generate reagent mapping data 170. In an embodiment, reagent mapping data 170 encodes how an atom or group of atoms of a reagent substructure pattern is mapped to an atom or group of atoms of a reagent molecule. FIG. 6 illustrates this stage or step of embodiment 100.

As can be seen in FIG. 6, in an embodiment, reagent connection data 620 is combined with reagent substructure pattern 610 to form a reaction map 550 according to the invention. Reaction map 550 is one form in which reaction data 170 can be stored for later retrieval. Reaction map 550 encodes data identifying that atom or node zero of reagent substructure pattern 610 maps to atom or node six of reagent connection data 620. Node six is labeled by number 624 in FIG. 6. Reaction map 550 also encodes data identifying that atom or node one of reagent substructure pattern 610 maps to atom or node seven of reagent connection data 620. Node seven is labeled by number 626 in FIG. 6. Data regarding atom or node five, labeled by number 622, is not needed in order to build products, and thus does not form a part of the data encoded by reaction map 550.

As will be known to a person skilled in the relevant art, reagent connection data 620 can be stored in the form of a reagent connection table. An example reagent connection table 560 is illustrated in FIG. 5.

In the third stage or step of embodiment 100, computer instructions 140, reagent connection data 160, and reagent mapping data 170 are combined to form library object 180. This is illustrated in FIG. 5. As illustrated in FIG. 5, in an embodiment, reagent mapping data 170 is stored as a number of reaction maps 550 and reagent connection data 160 is stored as a plurality of connection tables 560. In other embodiments, other structures may be used to store this information as would be known to a person skilled in the relevant art. For the connection table shown in FIG. 5, illustrative table entries indicate the number of bonds connecting particular atoms or groups of atoms.

As noted above, further features of embodiment 100 are described elsewhere herein. As will be understood by a person skilled in the relevant art given the description herein, library object 180 can be used to build products (e.g., generate product connection data) of a virtual combinatorial library "on-demand."

Figure 2:
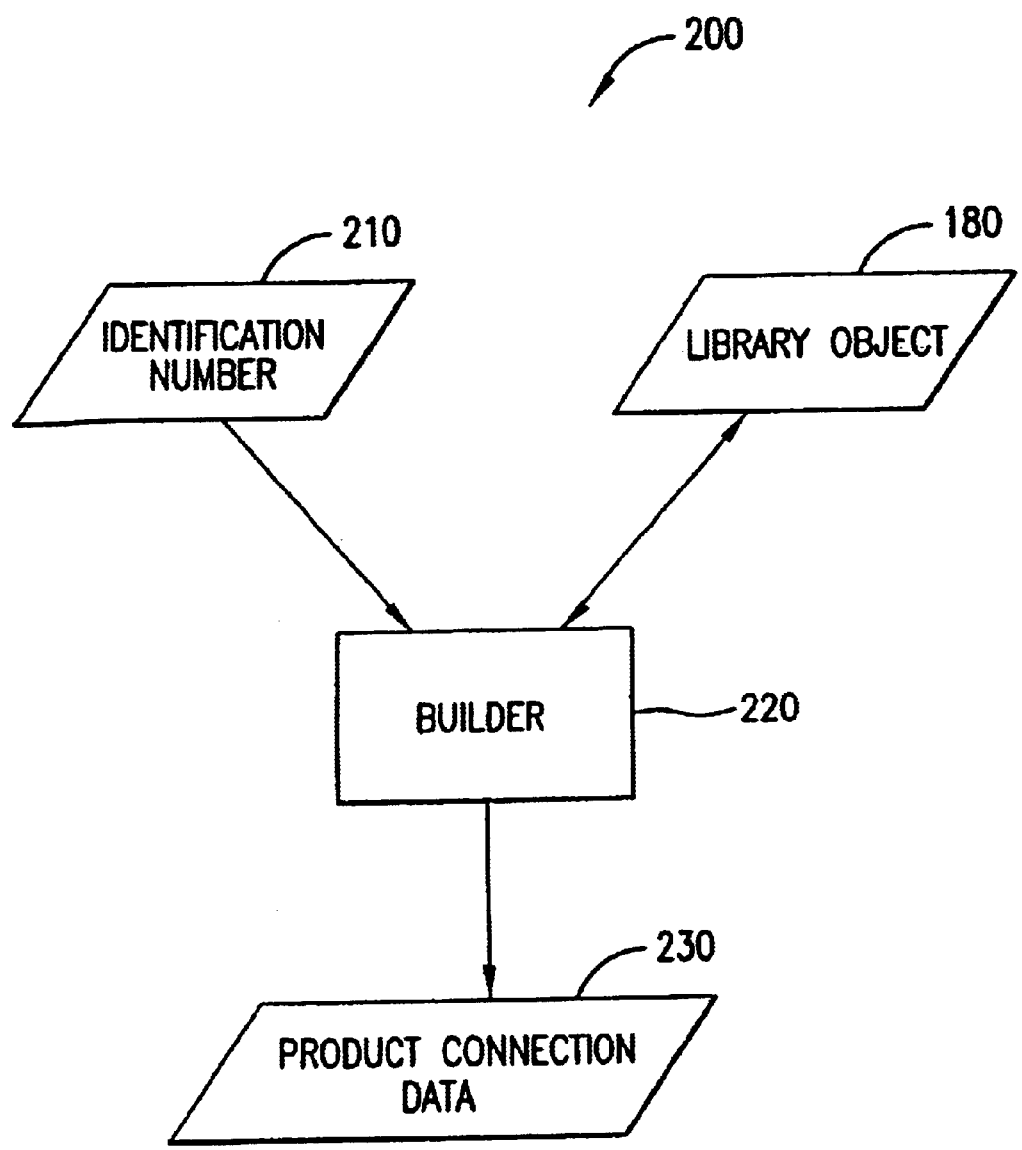
FIG. 2 illustrates a flowchart of an embodiment of the invention for building products of a virtual combinatorial library.

FIG. 2 illustrates an embodiment 200 for generating products or product connection data 230 according to the invention. Embodiment 200 involves using a builder 220 to operate on library object 180 and generate product connection data 230. The particular product connection data 230 generated by embodiment 200 is determined using an identification number 210.

As described herein, builder 220 is used to generate product connection data for the products of a virtual combinatorial library. Builder 220 uses compiled computer instructions 140 stored as a part of library object 180. Builder 220 operates on reagent mapping data 170 and reagent connection data 160 retrieved from library object 180. In an embodiment, the reagent mapping data 170 of library object 180 is stored as a plurality of reaction maps 550, and the reagent connection data 160 for a set of reagents is stored as a plurality of reagent connection tables 560. In an embodiment, the output of the builder is a product connection table for each product built. This is illustrated in FIG. 7.

As shown in FIG. 7, a product connection table 700 can be built from two reagent connection tables 702 and 704. Reagent connection table 702 stores connection data for a molecule A. Reagent connection table 704 stores connection data for a molecule B. In order to form product connection table 700, reagent connection tables 702 and 704 are combined as shown in FIG. 7 to form an extended connection table. As will be understood by a person skilled in the relevant art given the description herein, the combined connection table can be modified by adding and/or deleting bond entries, and by adding and/or deleting columns and rows that represent particular atoms or groups of atoms. These operations are controlled by computer instructions 140.

As described herein, in an embodiment of the invention computer instructions 140 provide explicit instructions that control how a processor is operated to assemble product molecule from reagents. For simplicity and speed, computer instructions 140 do not explicitly construct any intermediates that might be formed during a chemical reaction, but rather summarize the transformation of the input reagents directly into final products. This is further described below in the Library Construction section. As described herein, library object 180 includes all of the computer code and data needed to generate the products of a particular virtual combinatorial library.

As will be understood by a person skilled in the relevant art, data to build a product connection table is retrieved from library object 180 using, for example, a pointer to a memory location. In an embodiment, this pointer is identification number 210. In an embodiment, data needed to build a particular product is retrieved using a product identification number. In another embodiment, data needed to build a particular product is retrieved using an identification number associated with one or more reagents used to form the particular product. How to store and retrieve information from library object 180 using identification number 210 will be understood by a person skilled in the relevant art given the description of the invention herein.

Further features of embodiment 200 are also described elsewhere herein.

FIGS. 3A–B illustrate the steps of a computer method according to the invention for encoding and building products of a virtual combinatorial library. Method 300 can be implemented using the system and computer embodiments of the invention described herein. The features of method 300 are described both below with regard to the features of embodiments 100 and 200.

In step 310, at least one chemical transformation for generating product connection data 230 from reagent connection data 160 is encoded in computer readable form or script 110. As described above, in embodiments a chemical reaction or chemical transformation used to combine reagents and form products is encoded in a computer readable form. In an embodiment, a reaction scripting language (RSL) or scripting language is used to facilitate the encoding of chemical transformations. An RSL according to an embodiment of the invention is described below in the Library Construction section.

In step 320, at least one reagent substructure pattern 130 involved in forming the products of the virtual combinatorial library is encoded in computer readable form. This step is described in detail below in the Library Construction section.

In step 330, reagent mapping data 170 is generated from at least one reagent substructure pattern 130 (reaction map 550) and reagent connection data 160 for a set of reagents. FIG. 6 illustrates how this is performed. As can be seen in FIG. 6, in an embodiment, reagent connection data 620 is combined with reagent substructure pattern 610 by a mapper 150 to form a reaction map 550 according to the invention. Reaction map 550 is one form in which reaction data 170 can be stored for later retrieval.

In step 340, the encoded chemical transformation or transformations of step 310 is compiled into computer instructions 140. In an embodiment, compiler 120 is used to operate on script 110 and generate computer instructions 140. As described in more below in the Library construction section and elsewhere herein, computer instructions 140 are compiled computer instructions or computer logic for controlling the operation of a processor. FIG. 5 shows illustrative compiled computer instructions 540. Computer instructions 140 are used to control a processor and thereby generate product connection data from reagent connection data and reagent mapping data (e.g., reaction maps) according to the invention.

In step 350, a library object 180 according to the invention is generated. Library object 180 includes the compiled computer instructions 140 of step 340, the generated reagent mapping data 170 of step 330, and reagent connection data 160 for the set of reagents used to form the virtual combinatorial library. FIG. 5 illustrates an example of a library object 180 according to the invention.

In step 360, the library object is stored in a memory. The memory can be any memory, such as for example memory 1810 of FIG. 18. In an embodiment, the reagent connection data 160 for the set of reagents is stored as a plurality of reagent connection tables 560. In an embodiment of the invention, the reagent mapping data 170 is stored as a plurality of reaction maps 550.

In step 370, product connection data 230 is generated for a product of the virtual combinatorial library, using the compiled computer instructions 140 and reagent mapping data 170 and reagent connection data 160 retrieved from stored library object 180. In an embodiment, step 370 results in the generation of one or more product connection tables 700. In an embodiment, a build 220 is used to generate product connection data 230. The operation of step 370 is further described below in the Library Construction section.

As described herein, in an embodiment, at least one reaction map 550 and at least the reagent connection data 560 associated with the reagents is retrieved in step 370 and used to form a product of the virtual combinatorial library. In an embodiment, data from library object 180 is retrieved using a product identification number. In another embodiment, data is retrieved from the library object 180 using an identification number associated with at least one reagent. Further features of computer method 300 are described elsewhere herein.

FIG. 4 illustrates a computer method 400 for building products of a virtual combinatorial library according to an embodiment of the invention. The products of the virtual combinatorial library generated by method 400 are formed in accordance with a chemical reaction and selected reagents.

In step 410, a library object 180 is stored in a memory. In an embodiment, the library object 180 includes compiled chemical transformation computer instructions 140 that generate product connection data 230 from reagent connection data. The library object also includes reagent mapping data 170, and reagent connection data 160 for the set of reagents. In some embodiments, other information may be included in library object 180. For example, library object may include reagent pricing data and/or reagent availability data. Other types of data that would be useful to a user of a virtual combinatorial library can be included in library object 180, which would be known to a person skilled in the relevant art.

In step 420, product connection data 230 is generated for a product of the combinatorial library using the compiled computer instructions 140, reagent mapping data 170, and reagent connection data 160 retrieved from the stored library object 180. How this is done is described above with regard to embodiment 200, and below in the Library Construction section.

Further embodiments, features, and advantages of the present invention, as well as the structure and operation of the various embodiments of the present invention, are described in detail below.

Library Construction

As stated above, a reaction scripting language (RSL) or scripting language is used in embodiments of the invention to facilitate the encoding of chemical transformations and the enumeration of virtual libraries. The advantages of using a RSL include versatility, speed, and scalability.

In an embodiment, an RSL is designed as an extension of the Tool Command Language (Tcl) (see J. Ousterhout, Tcl and the Tk Toolkit, Addison-Wesley, ISBN 0-201-63337-X, 1994, which is incorporated by reference herein in its entirety), which has a fairly simple and human-readable syntax. Each combinatorial reaction is defined as a named Tcl procedure, thus providing a framework for creating libraries of common reaction schemes. RSL procedures are designed to be compilable into a sequence of parameterized function calls that are be executed in order to assemble the product structures. This facilitates fast, "on-demand" enumeration of combinatorial products.

When a reaction procedure is invoked, it generates a virtual combinatorial library from lists of reagents supplied in SD or SMILES format. In an embodiment, the generated library is stored in a compact form on disk and can be used at a later time for immediate access to any of the product structures. The names of the input reagent and output library files are passed as arguments to the Tcl reaction procedure. FIG. 8 illustrates an example of an RSL script according to an embodiment of the invention based on the reductive amination reaction.

Conceptually, an RSL procedure consists of three blocks: a definition block, an assembly instruction block and an execution trigger. The definition block defines the reagents and the product, and specifies the reactive patterns (reagent substructure patterns). The assembly instruction block provides explicit instructions on how to assemble the product molecule from the reagents, and what parts of the source molecules are eliminated in the process. For simplicity and speed, the assembly instructions do not explicitly construct any intermediates that might be formed during the reaction, but rather summarize the transformation of the input reagents directly into the final product. When the reaction script is executed, the assembly instructions are translated into a sequence of parameterized function calls. The assembly sequence is saved within the virtual library (library object), and every time a product needs to be assembled, this sequence is executed with the appropriate parameters. Lastly, the execution trigger is a statement that triggers the mapping of the reactive patterns onto the supplied sets of reagents, the compilation of the assembly instructions (computer instructions), and the storage of the virtual library into a file. Thus, our virtual library consists of structures of input reagents in their original form, maps of substructure patterns onto input reagents, and a sequence of compiled assembly instructions that should be executed in order to build the connection table of a product.

In an embodiment, RSL uses the SMARTS notation (see C. A. James et al., Daylight Theory Manual Daylight 4.71, Daylight Chemical Information Systems, Inc., 2000, http://www.daylight.com/dayhtml/doc/theory/theory.toc.html) to encode the substructural patterns that are involved in the reaction and must be present in order for the reagent to undergo the reaction. Each reagent can be defined using multiple patterns, and the order in which they are defined specifies the relative reactivity of the respective functional groups. For example, in the amination library in FIG. 8, lines 5 and 6 specify that both primary and secondary amines can react with an aldehyde. However, if both a primary and a secondary amine are present in the same molecule, the main product will be formed from the more reactive primary amine. By defining the SMARTS pattern corresponding to the primary amine before the secondary amine, one can ensure that the proper products will be assembled. Although it is possible to match both primary and secondary amines with a single SMARTS pattern, it would not be possible to differentiate their reactivity.

Sometimes it is difficult, if not impossible, to write a single SMARTS string that will match only the reactive substructure pattern. In this case, one can specify the substructures that are not reactive. For example, a simple amine pattern "C[NH2]" will match an amide as well, which is not susceptible to reductive amination. One can either modify the amine pattern as "[CX4][NH2]" or define the amide substructure "C(=O)[NH2]" and designate it as non-reactive. When non-reactive patterns are present, the invention looks for an overlap between the matched reactive and non-reactive substructures, and if they have at least one atom in common the reactive structure will be invalidated.

In an embodiment, after the reacting substructures of the reagents are defined, the remaining code of the reaction script encodes the instructions for product assembly. Once the product is defined (line 5 in FIG. 8), its name becomes a Tcl command that supports a series of molecular operations. These operations include addition of previously defined reagents, removal of atoms, addition and removal of bonds, changing of the bond order, etc. A list of the most frequently used operators for an embodiment is given in FIG. 9. Note that with the exception of the "add" command, which instructs the program to add the connection table of the reagent to the connection table of the product, the remaining assembly instructions require specification of individual atoms affected by the instructions. Individual atoms participating in the chemical transformation are referred to by the respective reagent's name and by the zero-based indices of the matching atoms in the respective SMARTS pattern. For example, the nitrogen atom from an "amine" reagent defined with the SMARTS pattern "C[NH2]" is referred to as "amine:1". Since SMARTS strings are written in a single line, all atom specifications defined in a pattern can be unambiguously numbered from left to right as they appear in the pattern string. Note that hydrogen atoms are part of the atom specification in SMARTS and therefore cannot be individually addressed. (See FIG. 9.)

Since the reagent definition can include multiple SMARTS patterns, it is important that the atoms referenced in the assembly instructions have the same indices in every pattern. For instance, the nitrogen atom in both the primary and secondary amines should have the same index (e.g. 1) if a single assembly instruction is to apply to both of them. Fortunately, it is always possible to write SMARTS specifications in the desired order using "ring closures" (numbers), disconnections (dots) and recursive atom environments. Moreover, in most cases, SMARTS encoding lends itself naturally to this requirement since multiple patterns are typically used to define variations of the same functionality, such as primary and secondary amines.

In embodiments of the invention, most if not all of the assembly instructions are obvious (e.g., "insert bond," "remove atom," "remove bond," "set atom charge," "set bond order," etc.) Note that there is no instruction to insert a single atom since all the atoms of a product must come from the reagents in accordance with the mass preservation law. Special instructions are also provided to define the stereochemical outcome of reactions controlled by steric approach preferences. In RSL embodiment, the major product of a stereochemical reaction can be specified, for example, in two ways: (1) via the configuration of the nascent chiral center(s), and (2) via the stereochemical character of a bond during addition and elimination. FIGS. 10–17 illustrate some examples of stereochemistry encoding in an RSL embodiment.

The stereochemical configuration of a formed chiral center can be identified as "unspecified," "racemic" or "inverse." "Unspecified" indicates that the exact configuration of the products is unknown or irrelevant (default). "Racemic" indicates that both the R and S stereoisomers are formed in comparable quantities. "Inverse" exchanges one of the chiral center's substituents during the reaction and inverts its configuration. The R/S assignment of the chiral center is automatically determined based on the original configuration and the CIP priority of the new substituent. In general, the stereochemical configuration of an atom can be specified by listing its substituents in clockwise order and designating the last substituent as an up (in front of the plane) or a down (behind the plane) wedge. In this case, the R/S assignment is based on the CIP priorities and order of the substituents. Alternatively, the R/S configuration of the chiral center could be explicitly specified, but this option is rarely used since the label depends on the CIP priorities of the individual building blocks.

Stereochemical ambiguity also emerges when the reaction mechanism involves multiple centers. For example, dehydrohalogenation leads to double bond formation via an anti elimination pathway, whereby two substituents are removed from opposite sides of the reduced single bond. The resulting double bond can be cis or trans depending on the original configuration of the bonded atoms. In an embodiment, RSL defines two keywords, "syn_product" and "anti_product," to specify whether an addition or elimination reaction proceeds in a syn or anti manner. Note that it is not always possible to identify a single product using these keywords. For completeness, the configuration of the double bond can also be explicitly specified as E or Z.

Finally, the "enumerate" statement triggers the creation of the virtual library. Although semantically simple, this statement is the complicated in its implementation. For scalability, the enumeration of the products must be implicit and must circumvent the creation of a connection table or even a record for every product in the library. This objective is accomplished by dividing the enumeration process in two steps. During the first step, the reacting and interfering functionalities are identified by matching the corresponding SMARTS patterns, and any reagents that are not compatible with the reaction transform are eliminated from further processing. This step involves mostly substructure searching, and scales linearly with the number of reagents that make up the virtual library. The second step involves the generation of products and is delayed until a particular product is requested. That is, the construction of the connection table of a particular product occurs only when its structure is needed for display or evaluation, and in many cases this never happens. In the next section, several methods to analyze a virtual library are described that require the enumeration of only a minor fraction of its members (products).

In order to accelerate the "on-demand" assembly of products, the mappings of the reactive groups matched by the SMARTS patterns are stored within the virtual library along with the compiled sequence of assembly operators. Thus, when the structure of a product is needed, no time is spent on substructure searching or parsing assembly instructions. This design and the speed of the underlying foundation classes and molecular perception algorithms upon which the invention software is based, enable the construction of products at a rate of 10,000 structures per second on a 800 MHz Pentium III processor, including full perception of valence, rings and aromaticity.

The reaction scripting language of the invention differs from other reaction languages, such as SMIRKS (see C. A. James et al., Daylight Theory Manual Daylight 4.71. Daylight Chemical Information Systems, Inc., 2000, http://www.daylight.com/dayhtml/doc/theory/theory.toc.html), in that it is designed specifically for generating virtual combinatorial libraries and not for reaction database searching. Thus, the RSL of the invention is less cryptic, provides more flexibility in encoding reaction transformations, and can be stored in a compiled form to allow ultra-fast product enumeration. In addition, in the RSL of the invention, SMARTS patterns of the reacting functionalities are not restricted as in SMIRKS, where bond queries are not allowed and atomic expressions cannot contain queries if the bond order or connectivity change (see C. A. James et al., Daylight Theory Manual Daylight 4.71. Daylight Chemical Information Systems, Inc., 2000, http://www.daylight.com/dayhtml/doc/theory/theory.toc.html).

Computer and Computer Program Product Embodiments of the Invention

As will be understood by a person skilled in the relevant arts given the description herein, FIG. 18 shows an example computer system 1800 that supports implementation of the present invention. The present invention may be implemented using hardware, software, firmware, or a combination thereof. It may be implemented in a computer system or other processing system. The computer system 1800 includes one or more processors, such as processor 1804. The processor 1804 is connected to a communication infrastructure 1806 (e.g., a bus or network). Various software embodiments can be described in terms of this exemplary computer system. After reading this description, it will become apparent to a person skilled in the relevant art how to implement the invention using other computer systems and/or computer architectures.

Computer system 1800 also includes a main memory 1808, preferably random access memory (RAM), and may also include a secondary memory 1810. The secondary memory 1810 may include, for example, a hard disk drive 1812 and/or a removable storage drive 1814, representing a floppy disk drive, a magnetic tape drive, an optical disk drive, etc. The removable storage drive 1814 reads from and/or writes to a removable storage unit 1818 in a well-known manner. Removable storage unit 1818 represents a floppy disk, magnetic tape, optical disk, etc. As will be appreciated, the removable storage unit 1818 includes a computer usable storage medium having stored therein computer software and/or data. In an embodiment of the invention, removable storage unit 1818 can contain input data to be projected.

Secondary memory 1810 can also include other similar means for allowing computer programs or input data to be loaded into computer system 1800. Such means may include, for example, a removable storage unit 1822 and an interface 1820. Examples of such may include a program cartridge and cartridge interface (such as that found in video game devices), a removable memory chip (such as an EPROM, or PROM) and associated socket, and other removable storage units 1822 and interfaces 1820, which allow software and data to be transferred from the removable storage unit 1822 to computer system 1800.

Computer system 1800 may also include a communications interface 1824. Communications interface 1824 allows software and data to be transferred between computer system 1800 and external devices. Examples of communications interface 1824 may include a modem, a network interface (such as an Ethernet card), a communications port, a PCMCIA slot and card, etc. Software and data transferred via communications interface 1824 are in the form of signals 1828 which may be electronic, electromagnetic, optical or other signals capable of being received by communications interface 1824. These signals 1828 are provided to communications interface 1824 via a communications path (i.e., channel) 1826. This channel 1826 carries signals 1828 and may be implemented using wire or cable, fiber optics, a phone line, a cellular phone link, an RF link and other communications channels. In an embodiment of the invention, signals 1828 can include input data to be projected.

Computer programs (also called computer control logic) are stored in main memory 1808 and/or secondary memory 1810. Computer programs may also be received via communications interface 1824. Such computer programs, when executed, enable the computer system 1800 to perform the features of the present invention as discussed herein. In particular, the computer programs, when executed, enable the processor 1804 to perform the features of the present invention. Accordingly, such computer programs represent controllers of the computer system 1800.

Conclusion

While various embodiments of the present invention have been described above, it should be understood that they have been presented by way of example, and not limitation. It will be apparent to persons skilled in the relevant art that various changes in detail can be made therein without departing from the spirit and scope of the invention. Thus the present invention should not be limited by any of the above-described exemplary embodiments, but should be defined only in accordance with the following claims and their equivalents.

What is claimed is:

1. A computer method for encoding and building products of a virtual combinatorial library, the products of the virtual combinatorial library being formed in accordance with a chemical reaction and selected reagents, the computer method comprising the steps of:

(1) encoding in computer readable form at least one chemical transformation for generating product connection data from reagent connection data;

(2) encoding in computer readable form at least one reagent substructure pattern involved in forming the products of the virtual combinatorial library;

(3) generating reagent mapping data from the at least one reagent substructure pattern and reagent connection data for a set of reagents;

(4) compiling into computer instructions the encoded at least one chemical transformation;

(5) generating a library object comprising the compiled computer instructions, the generated reagent mapping data, and the reagent connection data for the set of reagents;

(6) storing the library object in a memory; and (7) generating product connection data, using the compiled computer instructions and reagent mapping data and reagent connection data retrieved from the stored library object, for at least one product of the virtual combinatorial library.

2. The method of claim 1, wherein step (3) comprises: generating data that encodes how an atom of the at least one reagent substructure pattern is mapped to an atom of a reagent molecule.

3. The method of claim 1, wherein step (6) comprises: storing the reagent connection data for the set of reagents as a plurality of reagent connection tables.

4. The method of claim 1, wherein step (6) comprises: storing the reagent mapping data as a plurality of reaction maps.

5. The method of claim 1, wherein step (7) comprises: retrieving at least one reaction map and at least the reagent connection data associated with the reagents used to form the at least one product.

6. The method of claim 1, wherein step (7) comprises: retreiving data from the library object using a product identification number.

7. The method of claim 1, wherein step (7) comprises: retreiving data from the library object using an identification number associated with at least one reagent.

8. The method of claim 1, wherein step (7) comprises: generating a product connection table for the at least one product.

9. A computer method for building products of a virtual combinatorial library, the products of the virtual combinatorial library being formed in accordance with a chemical reaction and selected reagents, the computer method comprising the steps of:
  (1) storing a library object in a memory, the library object comprising:
    compiled chemical transformation computer instructions that generate product connection data from reagent connection data,
    reagent mapping data generated from at least one reagent substructure pattern and reagent connection data for a set of reagents, and
    reagent connection data for the set of reagents; and
  (2) generating product connection data, using the compiled computer instructions and reagent mapping data and reagent connection data retrieved from the stored library object, for at least one product of the virtual combinatorial library.

10. The method of claim 9, wherein step (1) comprises: storing data that encodes how an atom of the at least one reagent substructure pattern is mapped to an atom of a reagent molecule.

11. The method of claim 9, wherein step (1) comprises: storing the reagent connection data for the set of reagents as a plurality of reagent connection tables.

12. The method of claim 9, wherein step (1) comprises: storing the reagent mapping data as a plurality of reaction maps.

13. The method of claim 9, wherein step (2) comprises: retrieving at least one reaction map and at least the reagent connection data associated with the reagents used to form the at least one product.

14. The method of claim 9, wherein step (2) comprises: retreiving data from the library object using a product identification number.

15. The method of claim 9, wherein step (2) comprises: retrieving data from the library object using an identification number associated with at least one reagent.

16. The method of claim 9, wherein step (2) comprises: generating a product connection table for the at least one product.

17. A computer program product for encoding and building products of a virtual combinatorial library, the products of the virtual combinatorial library being formed in accordance with a chemical reaction and selected reagents, the computer program product comprising a computer useable medium having computer program logic recorded thereon for controlling a processor, the computer program logic comprising:
  a procedure that enables said processor to encode in computer readable form at least one chemical transformation for generating product connection data from reagent connection data;
  a procedure that enables said processor to encode in computer readable form at least one reagent substructure pattern involved in forming the products of the virtual combinatorial library;
  a procedure that enables said processor to generate reagent mapping data from the at least one reagent substructure pattern and reagent connection data for a set of reagents;
  a procedure that enables said processor to compile into computer instructions the encoded at least one chemical transformation;
  a procedure that enables said processor to generate a library object comprising the compiled computer instructions, the generated reagent mapping data, and the reagent connection data for the set of reagents;
  a procedure that enables said processor to store the library object in a memory; and
  a procedure that enables said processor to generate product connection data, using the compiled computer instructions and reagent mapping data and reagent connection data retrieved from the stored library object, for at least one product of the virtual combinatorial library.

18. The computer program product of claim 17, wherein the generated reagent mapping data comprises: data that encodes how an atom of the at least one reagent substructure pattern is mapped to an atom of a reagent molecule.

19. The computer program product of claim 17, wherein the reagent connection data for the set of reagents is stored as a plurality of reagent connection tables.

20. The computer program product of claim 17, wherein the reagent mapping data is stored as a plurality of reaction maps.

21. The computer program product of claim 17, wherein data from the library object is retrieved using a product identification number.

22. The computer program product of claim 17, wherein data from the library object is retrieved using an identification number associated with at least one reagent.

23. The computer program product of claim 17, wherein a product connection table is generated for the at least one product.

24. A computer program product for building products of a virtual combinatorial library, the products of the virtual combinatorial library being formed in accordance with a chemical reaction and selected reagents, the computer program product comprising a computer useable medium having computer program logic recorded thereon for controlling a processor, the computer program logic comprising:

a library object comprising:
  compiled chemical transformation computer instructions that generate product connection data from reagent connection data,
  reagent mapping data generated from at least one reagent substructure pattern and reagent connection data for a set of reagents, and
  reagent connection data for the set of reagents; and
a procedure that enables said processor to generate product connection data, using the compiled computer instructions and reagent mapping data and reagent connection data retrieved from the library object, for at least one product of the virtual combinatorial library.

25. The computer program product of claim 24, wherein the generated reagent mapping data comprises:
  data that encodes how an atom of the at least one reagent substructure pattern is mapped to an atom of a reagent molecule.

26. The computer program product of claim 24, wherein the reagent connection data for the set of reagents is stored as a plurality of reagent connection tables.

27. The computer program product of claim 24, wherein the reagent mapping data is stored as a plurality of reaction maps.

28. The computer program product of claim 24, wherein data from the library object is retrieved using a product identification number.

29. The computer program product of claim 24, wherein data from the library object is retrieved using an identification number associated with at least one reagent.

30. The computer program product of claim 24, wherein a product connection table is generated for the at least one product.

31. A computer system for encoding and building products of a virtual combinatorial library, the products of the virtual combinatorial library being formed in accordance with a chemical reaction and selected reagents, the computer system comprising:
  means for encoding in computer readable form at least one chemical transformation for generating product connection data from reagent connection data;
  means for encoding in computer readable form at least one reagent substructure pattern involved in forming the products of the virtual combinatorial library;
  means for generating reagent mapping data from the at least one reagent substructure pattern and reagent connection data for a set of reagents;
  means for compiling into computer instructions the encoded at least one chemical transformation;
  means for generating a library object comprising the compiled computer instructions, the generated reagent mapping data, and the reagent connection data for the set of reagents;
  means for storing the library object in a memory; and
  means for generating product connection data, using the compiled computer instructions and reagent mapping data and reagent connection data retrieved from the stored library object, for at least one product of the virtual combinatorial library.

32. A computer system for building products of a virtual combinatorial library, the products of the virtual combinatorial library being formed in accordance with a chemical reaction and selected reagents, the computer system comprising:
  means for storing a library object in a memory, the library object comprising:
    compiled chemical transformation computer instructions that generate product connection data from reagent connection data,
    reagent mapping data generated from at least one reagent substructure pattern and reagent connection data for a set of reagents, and
    reagent connection data for the set of reagents; and
  means for generating product connection data, using the compiled computer instructions and reagent mapping data and reagent connection data retrieved from the stored library object, for at least one product of the virtual combinatorial library.

* * * * *

UNITED STATES PATENT AND TRADEMARK OFFICE
CERTIFICATE OF CORRECTION

PATENT NO. : 6,678,619 B2
DATED : January 13, 2004
INVENTOR(S) : Victor S. Lobanov It is certified that error appears in the above-identified patent and that said Letters Patent is hereby corrected as shown below:

Title page,
Item [*] Notice, the patent term adjustment "106 days" should read -- 205 days --.

Signed and Sealed this

Seventeenth Day of August, 2004

JON W. DUDAS
*Acting Director of the United States Patent and Trademark Office*